(12) United States Patent
Komatsuki et al.

(10) Patent No.: US 8,377,458 B2
(45) Date of Patent: Feb. 19, 2013

(54) COOLING SENSATION AGENT COMPOSITION, SENSORY STIMULATION AGENT COMPOSITION AND USE OF THE SAME

(75) Inventors: Yasuhiro Komatsuki, Kanagawa (JP); Tomoko Yamamoto, Kanagawa (JP); Takashi Aida, Tokyo (JP); Kenya Ishida, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 128 days.

(21) Appl. No.: 12/898,939

(22) Filed: Oct. 6, 2010

(65) Prior Publication Data

US 2011/0081393 A1    Apr. 7, 2011

(30) Foreign Application Priority Data

Oct. 7, 2009   (JP) ................ 2009-233059

(51) Int. Cl.
*A61Q 5/02* (2006.01)
*A61Q 15/00* (2006.01)
*A61Q 13/10* (2006.01)

(52) U.S. Cl. ......... 424/401; 424/65; 424/70.1; 424/402; 426/538; 512/8

(58) Field of Classification Search ............... None
See application file for complete search history.

(56) References Cited

U.S. PATENT DOCUMENTS

| | | | |
|---|---|---|---|
| 3,312,226 A | 4/1967 | Bavley et al. | |
| 5,753,609 A | 5/1998 | Nakatsu et al. | |
| 8,026,277 B2 * | 9/2011 | Aida et al. | 514/506 |
| 8,071,531 B2 * | 12/2011 | Aida et al. | 512/23 |
| 2007/0225378 A1 * | 9/2007 | Ishida et al. | 514/715 |
| 2009/0275669 A1 * | 11/2009 | Aida et al. | 514/772 |
| 2011/0117147 A1 * | 5/2011 | Ishida et al. | 424/401 |

FOREIGN PATENT DOCUMENTS

| | | |
|---|---|---|
| EP | 0 816 322 A1 | 1/1998 |
| EP | 1 077 251 A1 | 2/2001 |
| JP | 45-026872 B | 9/1970 |
| JP | 08-225564 | 9/1996 |
| JP | 10-095752 | 4/1998 |
| JP | 2000-096443 | 4/2000 |
| JP | 2006-161226 | 6/2006 |
| JP | 2009-520701 | 5/2009 |
| WO | WO 94/06441 | 3/1994 |
| WO | WO 95/04809 | 2/1995 |
| WO | WO 97/16523 | 5/1997 |
| WO | WO 2007/071085 A1 | 6/2007 |

OTHER PUBLICATIONS

Herrmann, A., et al., "Controlled Release of Volatiles under Mild Reaction Conditions: From Nature to Everyday Products", Agnew. Chem. Int. Ed., pp. 5836-5863, 2007, vol. 46, Wiley-VCH Verlag GmbH & Co. KGaA Weinham.

* cited by examiner

*Primary Examiner* — Jyothsna Venkat
(74) *Attorney, Agent, or Firm* — McDermott Will & Emery LLP

(57) ABSTRACT

Disclosed is a cooling sensation agent composition or sensory stimulation agent composition which contains at least one of diester compounds of dicarboxylic acid represented by the formula (1) wherein A represents $CH_2$ or $CH=CH$, n represents an integer of 0 to 4 when A is $CH_2$, or 1 when A is $CH=CH$, B is an alcohol residue having 10 to 18 carbon atoms and containing a para-menthane skeleton, which may have a substituent, and C is an alcohol residue having 6 to 18 carbon atoms, which may have a substituent as well as a flavor or fragrance composition, a beverage, a food product, a perfume or cosmetic product, a toiletry product, daily utensil products or groceries, a fiber, a fiber product, clothes, clothing or a medicine, wherein the cooling sensation agent composition or the sensory stimulation agent composition is compounded.

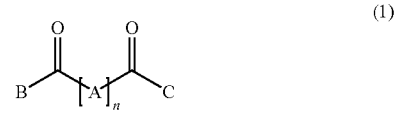

(1)

18 Claims, No Drawings

US 8,377,458 B2

COOLING SENSATION AGENT COMPOSITION, SENSORY STIMULATION AGENT COMPOSITION AND USE OF THE SAME

FIELD OF THE INVENTION

The present invention relates to novel esters of dicarboxylic acid, a cooling sensation agent composition containing the same, a sensory stimulation agent composition containing the cooling sensation agent composition as well as a flavor or fragrance composition, a beverage, a food product, a perfume or cosmetic product, a toiletry product, a daily utensil product or grocery, fibers, fiber products, clothes, clothing or a medicine, which contains the cooling sensation agent composition or the sensory stimulation agent composition and a method for producing the same. The present invention also relate to a method for providing long-lasting cooling sensation or a cool refreshment processing method using the cooling sensation agent composition or the sensory stimulation agent composition.

BACKGROUND OF THE INVENTION

A cooling sensation agent that endows the skin, oral cavity, nose and throat of a person with a refresh feeling (refresh sensation) and cool feeling (cooling sensation), that is cooling sensation effect, is used in various products such as toothpastes, confectioneries such as chewing gums and candies, tobacco, cataplasms, bath agents and cosmetics. Menthol, which is the representative cooling sensation agent material, has an excellent cooling sensation effect. However as menthol is highly volatile, the cooling sensation effect thereof does not last so long. Therefore, studies have been carried out to maintain a cooling sensation action for a long period of time. Examples of the compounds having been developed to maintain the cooling sensation for a prolonged period of time include menthoxypropanediol that is glycerin ether of menthol, lactic ester of menthol, ethylene glycol ether of menthol and the like.

However, under influence of recent global warming, there has been a demand for cool feeling processing of clothing such as clothes and the like to make people feel more comfortable even in hot summer. Most cooling sensation agents including menthol, however, are highly volatile and also highly water-soluble, and thus, the cool feeling processing of clothes and the like by use of the cooling sensation agents often results in loss of the action within a short period of time. For example, even if a cooling sensation agent is compounded with a detergent or a softener, the cooling sensation agent hardly remains on the clothing fiber after washing because of its water solubility and further, no cooling sensation agent remains after drying because of its high volatility.

To solve these problems, sustained-release cooling sensation agents utilizing a chemical change has been developed. For example, a method for giving a refresh feeling to gas to be breathed at smoking by releasing a cooling sensation agent, menthol due to thermal decomposition of chlorocarbonic esters or carbonic esters contained in tobacco on combustion of tobacco (U.S. Pat. No. 3,312,226), a method for releasing a fragrance component by decomposition of carbonic esters on the skin to elongate the diffusion period of the fragrance (JP 10-95752 A), a method for releasing a fragrance due to decomposition of orthoesters by perspiration on the skin (WO 94/06441 A), and the like are mentioned. In addition to them, there are known many patents that utilize release of a fragrance molecule by decomposition of a fragrance precursor based on a chemical change or an enzyme reaction (JP 45-26872 B, EP 1077251 A, WO 95/04809 A, WO 97/16523 A, JP 8-225564 A, JP 2009-520701 A, and Angew. Chem. Int. Ed, 2007, 46, 5836-5863). JP 45-26872 B, for example, discloses cosmetics in which monomenthyl or dimenthyl esters of dicarboxylic acid is contained. The esters in the cosmetics are decomposed by an ester-hydrolyzing enzyme present in a skin or an alkali included in an alkaline cosmetic that is already applied on the skin to release menthol. However, it is not known that the aforementioned dimenthyl esters of dicarboxylic acid themselves have an excellent cooling sensation effect. In addition, when a precursor of a flavor or fragrance compound is used, there are still some problems that quite a long time is required till the decomposition reaction of the precursor starts and a flavor or fragrance compound is released after adhesion of the precursor to clothes or a skin, the strength of cooling sensation is significantly weak, and so on. Thus, it is not a fundamental solution.

Other studies on the method for providing clothes with cooling action, for example, using microcapsules or the like have been conducted, and many patent applications have been filed. Examples thereof include a fiber processing method by use of microcapsules containing mint oil or l-menthol (JP 2000-96443 A), a fiber processing method by use of a microcapsulated substance which melts at a temperature not higher than the body temperature, so that the substance gives persons a cooling action reversibly by latent heat when contacting with skin (JP 2006-161226 A), or the like. However, they have also problems. That is, in the former method, processed clothes, of course, loses its action after releasing of all cooling sensation agent by destruction of the microcapsules, and it is actually impossible to re-process the clothes at home. Further, because the stage of releasing the cooling sensation agent by destruction of the microcapsules is the rate-determining step in this method, similar to a chemical reaction, it is not currently at the technological level where the cooling action can be provided to persons just after wearing of the clothes. In the latter method which relies on phase transition between solid and liquid, the cooling action cannot be provided to persons in constantly hot areas where the microcapsulated substance does not return to the solid state after melting.

An object of the present invention is to provide a cooling sensation agent composition by which the conventional problems described above are solved, i.e., to provide a cooling sensation agent composition which shows the long-lasting cooling action for an extended period of time.

Another object of the present invention is to provide a sensory stimulation agent composition which contains the cooling sensation agent composition.

Still another object of the present invention is to provide a flavor or fragrance composition, a beverage, a food product, a perfume or cosmetic product, a toiletry product, daily utensil products and groceries, and a medicine, which contain the cooling sensation agent composition or the sensory stimulation agent composition, and also a production method of the same.

Further, still another object of the present invention is to provide a method for providing a prolonged cooling action by applying one of the aforementioned products containing the cooling sensation agent composition or the sensory stimulation agent composition directly onto a skin or a scalp, administering it into an oral cavity, or applying it on fibers, a fiber product, clothes or clothing; or a cool refreshment processing method of fibers, a fiber product, clothes or clothing by compounding a cooling sensation agent composition or the sensory stimulation agent composition with those or processing those with a cooling sensation agent composition or the sensory stimulation agent composition.

Furthermore, another object of the present invention is to provide novel diesters of dicarboxylic acid.

As a result of intensive studies to solve the problems described above, inventors of the invention found that a diester compound of dicarboxylic acid where at least one of the diester includes an alcohol residue having a para-menthane skeleton, which may have a substituent, but not all of the alcohol residues are a menthol residue, has an excellent and long-lasting cooling sensation effect. In addition, the inventors also found that the diesters may easily remain in clothes when it is compounded with a detergent, a fabric softener or the like and the clothes are washed using the detergent or rinsed using the softer, and the clothes after washing or rinsing exhibit a gentle and long-lasting cooling sensation at the time of wearing or after the wearing. Further, the inventors found that a long-lasting cool refreshing action was obtained even when the diester compound is compounded for a beverage, a food product, a perfume or cosmetic product, a toiletry product, daily utensil products or groceries, tobacco, a medicine and the like. The present invention was made based on these findings.

SUMMARY OF THE INVENTION

Specifically, the present invention relates to a cooling sensation agent composition and a sensory stimulation agent composition as well as the flavor or fragrance agent composition containing the compositions. The present invention also relates to a beverage, a food product, a perfume or cosmetic product, a toiletry product, daily utensil products or groceries, a fiber, a fiber product, clothes, clothing or the medicine, a method for producing the same, a method for providing a long-lasting cool refreshing action, and a cool refreshment processing method for a fiber, a fiber product, clothes or clothing described in the followings items [1] to [16]. Further, the present invention also relates to novel diester compounds of dicarboxylic acid described in the followings items [17] to [20].

[1] A cooling sensation agent composition which contains at least one of diester compounds of dicarboxylic acid represented by the formula (1):

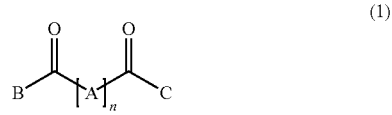

(1)

wherein, A represents $CH_2$ or $CH=CH$, n represents an integer of 0 to 4 when A is $CH_2$, or 1 when A is $CH=CH$, B is an alcohol residue having 10 to 18 carbon atoms and containing a para-menthane skeleton, which may have a substituent, and C is an alcohol residue having 6 to 18 carbon atoms, which may have a substituent.

[2] The cooling sensation agent composition described in above item [1], wherein C in the formula (1) is an alcohol residue having a para-menthane skeleton, which may have a substituent.

[3] The cooling sensation agent composition described in above item [2], wherein B and C in the formula (1) are not the same residue.

[4] The cooling sensation agent composition described in any one of above items [1] to [3], wherein the alcohol residue for B or B and C in the formula (1) having a para-menthane skeleton, which may have a substituent, is one selected from alcohol residues consisting of l-menthol, l-isopulegol, 3-(l-menthoxy)propane-1,2-diol, 2-(l-menthoxy)ethan-1-ol, 3-(l-menthoxy)propan-1-ol, 2-methyl-3-(l-menthoxy)propane-1,2-diol and para-menthane-3,8-diol.

[5] The cooling sensation agent composition described in any one of above items [1] to [4], wherein the diester compounds of dicarboxylic acid represented by the formula (1) have ClogP of 3.0 or more and the molecular weight of 250 to 600.

[6] The cooling sensation agent composition described in any one of above items [1] to [5], which further comprises at least one kind of cooling sensation substances other than the compounds corresponding to the formula (1).

[7] The cooling sensation agent composition described in above item [6], wherein the cooling sensation substances other than the compounds corresponding to the formula (1) are menthol, menthone, camphor, pulegol, isopulegol, cineole, mint oil, peppermint oil, spearmint oil, eucalyptus oil, 3-(l-menthoxy)propane-1,2-diol, N-alkyl-p-menthane-3-carboxamide, 2-methyl-3-(l-menthoxy)propane-1,2-diol, p-menthane-3,8-diol, 2-(l-menthoxy)ethan-1-ol, 3-(l-menthoxy)propan-1-ol, 4-(l-menthoxy)butan-1-ol, menthyl 3-hydroxybutanoate, menthyl lactate, menthone glycerin ketal, N-methyl-2,2-isopropylmethyl-3-methylbutane amide and menthyl glyoxylate.

[8] A sensory stimulation agent composition which contains the cooling sensation agent composition described in any one of above items [1] to [7].

[9] The sensory stimulation agent composition described in above item [8], which further comprises at least one kind of warming and pungent substances.

[10] The sensory stimulation agent composition described in above item [9], wherein the warming and pungent substances are vanillyl ethyl ether, vanillyl propyl ether, vanillin propylene glycol acetal, ethylvanillin propylene glycol acetal, capsaicin, gingerol, vanillyl butyl ether, 4-(l-menthoxymethyl)-2-(3'-methoxy-4'-hydroxy-phenyl)-1,3-dioxolane, pepper oil, pepper oleoresin, ginger oleoresin, nonylic acid vanillylamide, jamboo oleoresin, Zanthoxylum Piperitum Peel Extract, sanshool-I, sanshool-II, sanshoamide, black pepper extract, chavicine, piperine and spilanthol.

[11] A flavor or fragrance composition, a beverage, a food product, a perfume or cosmetic product, a toiletry product, daily utensil products or groceries, a fiber, a fiber product, clothes, clothing or a medicine, which comprises the cooling sensation agent composition or the sensory stimulation agent composition described in any one of above items [1] to [10].

[12] A method for providing a long-lasting cooling sensation effect, which comprises applying directly any one of products described in above item [11] onto a skin or a scalp, administering any one of them into an oral cavity, or applying any one of them to a fiber, a fiber product, clothes or clothing.

[13] A flavor or fragrance agent composition described in above item [11], wherein the content of the cooling sensation agent composition or the sensory stimulation agent composition is 0.0001 to 90% by mass.

[14] A beverage, a food product, a perfume or cosmetic product, a toiletry product, daily utensil products or groceries, a fiber, a fiber product, clothes, clothing or a medicine described in above item [11], wherein the content of the cooling sensation agent composition or the sensory stimulation agent composition is $1 \times 10^{-7}$ to 20% by mass.

[15] A cool refreshment processing method for a fiber, a fiber product, clothes or clothing, which comprises compounding the cooling sensation agent composition or the sensory stimulation agent composition described in any one of above items [1] to [10] to a fiber, a fiber product, clothes or clothing, or processing a fiber, a fiber product, clothes or clothing with the cooling sensation agent composition or the sensory stimulation agent composition described in any one of above items [1] to [10].

[16] A method for producing a flavor or fragrance composition, a beverage, a food product, a perfume or cosmetic product, a toiletry product, daily utensil products or groceries, a fiber, a fiber product, clothes, clothing or a medicine, which comprises compounding the cooling sensation agent composition or the sensory stimulation agent composition described in any one of above items [1] to [10] with a beverage, a food product, a perfume or cosmetic product, a toiletry product, daily utensil products or groceries, a fiber, a fiber product, clothes, clothing or a medicine.

[17] Diester compounds of dicarboxylic acid represented by the formula (1'):

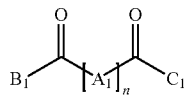

(1')

wherein, $A_1$ represents $CH_2$, n represents an integer of 0 to 4, $B_1$ is an alcohol residue of an alcohol having 10 to 18 carbon atoms and containing a para-menthane skeleton, which may have a substituent, and $C_1$ is an alcohol residue of an alcohol having 6 to 18 carbon atoms, which may have a substituent, however when $B_1$ or $C_1$ is an alcohol residue of menthol, another is not an alcohol residue of menthol.

[18] The diester compounds of dicarboxylic acid described in above item [17], wherein $C_1$ in the formula (1') is an alcohol residue of an alcohol having a para-menthane skeleton, which may have a substituent.

[19] The diester compounds of dicarboxylic acid described in above item [18], wherein $B_1$ and $C_1$ in the formula (1') are not the same residue.

[20] The diester compounds of dicarboxylic acid described in any one of above items [17] to [19], wherein the alcohol residue for $B_1$ or $B_1$ and $C_1$ in the formula (1') having a para-menthane skeleton, which may have a substituent, is any one selected from alcohol residues of l-menthol, l-isopulegol, 3-(l-menthoxy)propane-1,2-diol, 2-(l-menthoxy)ethan-1-ol, 3-(l-menthoxy)propan-1-ol, 2-methyl-3-(l-menthoxy)propane-1,2-diol and para-menthane-3,8-diol.

The present invention provides a cooling sensation agent composition imparting a long-lasting cooling sensation effect and a sensory stimulation agent composition with a long-lasting cooling sensation effect containing the cooling sensation agent composition. Further, in the invention, by compounding the cooling sensation agent composition or the sensory stimulation agent composition with a flavor or fragrance composition, a beverage, a food product, a perfume or cosmetic product, a toiletry product, daily utensil products or groceries, a fiber, a fiber product, clothes, clothing and a medicine, it is possible to prepare the products providing the cooling sensation effect or the sensation stimulating effect, which lasts for a long period of time. Furthermore, when these products are directly applied onto a skin or a scalp or administered into an oral cavity, a cooling sensation effect or the sensation stimulating effect lasting for a long period of time can be given to the skin, the scalp or the oral cavity, etc. and when they are applied to a fiber, a fiber product, clothes or clothing, etc., a gentle cooling sensation effect is given at the time of wearing and also a gentle prolonged cooling sensation effect is given even after wearing. Further, when the cooling sensation agent composition or the sensory stimulation agent composition is compounded with a detergent, a fabric softener or the like, a gentle or prolonged gentle cooling effect can be given at the time of wearing the clothes or clothing after washing or rinsing using the detergent, the fabric softener or the like and after wearing the cloth, in the present invention. Furthermore, the present invention provides novel compounds.

DETAILED DESCRIPTION OF THE INVENTION

Herein after, the invention will be described in more detail. As described above, the invention relates to a cooling sensation agent composition, a sensory stimulation agent composition as well as a flavor or fragrance composition, a beverage, a food product, a perfume or cosmetic product, a toiletry product, daily utensil products or groceries, a fiber, a fiber product, clothes, clothing or a medicine containing these compositions, a method for producing the same, a method for providing a long-lasting cooling sensation effect, a cool refreshment processing method for a fiber, a fiber product, clothes, and clothing and novel compounds. First, the cooling sensation agent composition of the invention will be explained in detail.

The cooling sensation agent composition of the invention contains at least one of diester compounds of dicarboxylic acid that are represented by the following Formula (1).

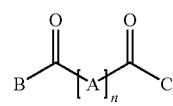

(1)

wherein, A represents $CH_2$ or $CH=CH$, n represents an integer of 0 to 4 when A is $CH_2$, or 1 when A is $CH=CH$, B is an alcohol residue having 10 to 18 carbon atoms and containing a para-menthane skeleton, which may have a substituent, and C is an alcohol residue having 6 to 18 carbon atoms, which may have a substituent.

Meanwhile, as described in "Background of the invention", there are already well known cosmetics containing dimenthyl esters of a dicarboxylic acid such as phthalic acid, succinic acid, maleic acid, and adipic acid, which are the compounds closely related to the compounds represented by the formula (1), and that fresh feeling can be provided after putting make-up using the cosmetics (JP-B 45-26872). However, these dimenthyl esters of dicarboxylic acid release menthol due to a degradation reaction by an alkali or an enzyme present in a skin to give cool feeling. In other words, the dimenthyl esters of dicarboxylic acid are precursors of a substance which gives cool feeling and it is not known from the document that the dimenthyl esters of dicarboxylic acid themselves give an excellent cooling sensation effect. In addition, it is not disclosed in the document at all that an excellent long-lasting cooling sensation effect can be given by their use in combination with other sensory stimulating component like a cooling sensation agent, a warming agent and the like.

Furthermore, the dimenthyl diesters having a symmetrical construction are generally in a wax state with a high viscosity or in a solid form, and are hard to handle and have a poor yield when they are compounded with a product. Surprisingly, however, non-symmetric diesters of dicarboxylic acid like the diesters of dicarboxylic acid represented by the above Formula (1) are generally oily substances having a low viscosity and can be easily compounded with a flavor or fragrance and other various products and have a good yield. Further, they themselves have a excellent long-lasting cooling sensation effect compared to the dimenthyl esters described above, and also by using it in combination with other sensory stimulating component such as a cooling sensation agent, a warming agent and the like, an excellent long-lasting cooling sensation effect can be given.

Furthermore, as described above, the document shown in the prior art describes dimenthyl esters in which both two alcohol residues are menthol in regard to the dicarboxylic esters represented by the formula (1), however there exists no description of a dicarboxylic ester compound or dicarboxylic ester compound mixture excluding the above dimenthyl esters, i.e., a dicarboxylic ester compound which contains one selected from alcohol residues of alcohols with 10 to 18 carbon atoms and a para-menthane skeleton, which may have a substituent, such as l-menthol, l-isopulegol, 3-(l-menthoxy)propane-1,2-diol, 2-(l-menthoxy)ethan-1-ol, 3-(l-menthoxy)propan-1-ol, 2-methyl-3-(l-menthoxy)propane-1,2-diol, para-menthane-3,8-diol and the like and one selected from alcohol residues with 6 to 18 carbon atoms. Therefore, these are novel substances.

Volatility and oleophilicity of the compounds represented by the formula (1) will be disclosed below. Volatility of a compound is significantly affected by a functional group attached to a molecule of the compound. On the other hand, flash point or boiling point can be increased by increasing the molecular weight and a compound having a molecular weight of approximately 250 to 600, preferably 300 to 500, is a less volatile compound. In addition, a compound having a molecular weight of more than 600 shows almost no cool feeling. For that reason, the compounds represented by the formula (1) used in the cooling sensation agent composition of the present invention preferably have a molecular weight in the range of preferably 250 to 600, and more preferably 300 to 600.

The oleophilicity of a compound is influenced significantly by the functional group attached to a molecule of the compound and the number of carbons thereof; and presence of a hydroxyl group leads to decrease of oleophilicity, while increase in the number of carbons leads to increase of oleophilicity. Water/octanol distribution coefficient (ClogP) is normally used as the indicator of oleophilicity. Menthol, for example, has a ClogP of 2.5, while dimenthyl carbonate having not only the hydroxyl group blocked with carbonic esters but also an increased molecular weight has a ClogP of 4.5, and thus, dimenthyl carbonate is highly oleophilic and less soluble in water. The ClogP values of the compounds of the formula (1) used in the cooling sensation agent composition of the present invention are preferably in the range of 3.0 or more, more preferably 4.0 or more.

As alcohols which are used for forming alcohol residues of B in the formula (1) of the invention, which have 10 to 18 carbon atoms and a para-menthane skeleton, and may have a substituent, e.g., a hydroxyl group, an ether group and the like, there may be preferably exemplified l-menthol, l-isopulegol, 3-(l-menthoxy)propane-1,2-diol, 2-(l-menthoxy)ethan-1-ol, 3-(l-menthoxy)propan-1-ol, 2-methyl-3-(l-menthoxy)propane-1,2-diol and para-menthane-3,8-diol.

In addition, as alcohols which are used for forming alcohol residues of C in the formula (1) which have 6 to 18 carbon atoms and may have a substituent, e.g., a hydroxyl group, an ether group and the like, there may be exemplified alcohols having 10 to 18 carbon atoms and a para-menthane skeleton, which may have a substituent, and other alcohols except for the aforementioned alcohols, that are linear, branched or cyclic alcohols having 10 to 18 carbon atoms, which may have an unsaturated bond, an ether group, an aromatic ring and/or an fused ring derived from the aromatic ring.

As alcohols having 10 to 18 carbon atoms and a para-menthane skeleton, which may have a substituent and are used for forming alcohol residues having 6 to 18 carbon atoms, which may have a substituent, of C in the formula (1), there may be preferably exemplified l-menthol, l-isopulegol, 3-(l-menthoxy)propane-1,2-diol, 2-(l-menthoxy)ethan-1-ol, 3-(l-menthoxy)propan-1-ol, 2-methyl-3-(l-menthoxy)propane-1,2-diol and para-menthane-3,8-diol, similar to B.

As liner or branched saturated alcohols among the linear or cyclic alcohols having 6 to 18 carbon atoms, which may have an unsaturated bond, an ether group, an aromatic ring and/or an fused ring derived from an aromatic ring in C of the formula (1), there may be exemplified, but not particularly limited to, hexanol, heptanol, octanol, nonanol, decanol, undecanol, dodecanol, tridecanol, tetradecanol, 2-methylhexanol, 3-methylhexanol, 4-methylhexanol, 5-methylhexanol, 2-methylheptanol, 3-methylheptanol, 4-methylheptanol, 5-methylheptanol, 6-methylheptanol, 2-methyloctanol, 3-methyloctanol, 4-methyloctanol, 5-methyloctanol, 6-methyloctanol, 7-methyloctanol, 2-methylnonanol, 3-methylnonanol, 4-methylnonanol, 5-methylnonanol, 6-methylnonanol, 7-methylnonanol, 8-methylnonanol, 2-methyldecanol, 3-methyldecanol, 4-methyldecanol, 5-methyldecanol, 6-methyldecanol, 7-methyldecanol, 8-methyldecanol, 9-methyldecanol, 2,3-dimethylpentanol, 2,4-dimethylpentanol, 2,2-dimethylpentanol, 3,3-dimethylpentanol, 3,4-dimethylpentanol, 4,4-dimethylpentanol, 2,2-dimethylhexanol, 2,3-dimethylhexanol, 2,4-dimethylhexanol, 2,5-dimethylhexanol, 3,3-dimethylhexanol, 3,4-dimethylhexanol, 3,5-dimethylhexanol, 4,4-dimethylhexanol, 4,5-dimethylhexanol, 5,5-dimethylhexanol, 2,2-dimethylheptanol, 2,3-dimethylheptanol, 2,4-dimethylheptanol, 2,5-dimethylheptanol, 2,6-dimethylheptanol, 3,3-dimethylheptanol, 3,4-dimethylheptanol, 3,5-dimethylheptanol, 3,6-dimethylheptanol, 4,4-dimethylheptanol, 4,5-dimethylheptanol, 4,6-dimethylheptanol, 5,5-dimethylheptanol, 5,6-dimethylheptanol, 6,6-dimethylheptanol, 2,2-dimethyloctanol, 2,3-dimethyloctanol, 2,4-dimethyloctanol, 2,5-dimethyloctanol, 2,6-dimethyloctanol, 2,7-dimethyloctanol, 3,3-dimethyloctanol, 3,4-dimethyloctanol, 3,5-dimethyloctanol, 3,6-dimethyloctanol, 3,7-dimethyloctanol, 4,4-dimethyloctanol, 4,5-dimethyloctanol, 4,6-dimethyloctanol, 4,7-dimethyloctanol, 5,5-dimethyloctanol, 5,6-dimethyloctanol, 5,7-dimethyloctanol, 6,6-dimethyloctanol, 6,7-dimethyloctanol, 7,7-dimethyloctanol, 2,2-dimethylnonanol, 2,3-dimethylnonanol, 2,4-dimethylnonanol, 2,5-dimethylnonanol, 2,6-dimethylnonanol, 2,7-dimethylnonanol, 2,8-dimethylnonanol, 3,3-dimethylnonanol, 3,4-dimethylnonanol, 3,5-dimethylnonanol, 3,6-dimethylnonanol, 3,7-dimethylnonanol, 3,8-dimethylnonanol, 4,4-dimethylnonanol, 4,5-dimethylnonanol, 4,6-dimethylnonanol, 4,7-dimethylnonanol, 4,8-dimethylnonanol, 5,5-dimethylnonanol, 5,6-dimethylnonanol, 5,7-dimethylnonanol, 5,8-dimethylnonanol, 6,6-dimethylnonanol, 6,7-dimethylnonanol, 6,8-dimethylnonanol, 7,7-dimethylnonanol, 7,8-dimethylnonanol, 8,8-dimethylnonanol, 3-methyl-2-hexanol, 4-methyl-2-hexanol, 5-methyl-2-hexanol, 3-methyl-2-heptanol, 4-methyl-2-heptanol, 5-methyl-2-heptanol, 6-methyl-2-heptanol, 3-methyl-2-octanol, 4-methyl-2-octanol, 5-methyl-2-octanol, 6-methyl-2-octanol, 7-methyl-2-octanol, 3-methyl-2-nonanol, 4-methyl-2-nonanol, 5-methyl-2-nonanol, 6-methyl-2-nonanol, 7-methyl-2-nonanol, 8-methyl-2-nonanol, 3-methyl-2-decanol, 4-methyl-2-decanol, 5-methyl-2-decanol, 6-methyl-2-decanol, 7-methyl-2-decanol, 8-methyl-2-decanol, 9-methyl-2-decanol, 3,3-dimethyl-2-pentanol, 3,4-dimethyl-2-pentanol, 4,4-dimethyl-2-pentanol, 3,3-dimethyl-2-hexanol, 3,4-dimethyl-2-hexanol, 3,5-dimethyl-2-hexanol, 4,4-dimethyl-2-hexanol, 4,5-dimethyl-2-hexanol, 5,5-dimethyl-2-hexanol, 3,3-dimethyl-2-heptanol, 3,4-dimethyl-2-heptanol, 3,5-dimethyl-2-heptanol, 3,6-dimethyl-2-heptanol, 4,4-dimethyl-2-heptanol, 4,5-dimethyl-2-heptanol, 4,6-dimethyl-2-heptanol, 5,5-dimethyl-2-heptanol, 5,6-dimethyl-2-heptanol, 6,6-dimethyl-2-heptanol, 3,3-dimethyl-2-octanol, 3,4-dimethyl-2-octanol, 3,5-dimethyl-2-octanol, 3,6-dimethyl-2-octanol, 3,7-dimethyl-2-octanol, 4,4-dimethyl-2-octanol, 4,5-dimethyl-2-octanol, 4,6-dimethyl-2-octanol, 4,7-dimethyl-2-octanol, 5,5-dimethyl-2-octanol, 5,6-dimethyl-2-octanol, 5,7-dimethyl-2-octanol, 6,6-dimethyl-2-octanol, 6,7-dimethyl-2-octanol, 7,7-dimethyl-2-octanol, 3,3-dimethyl-2-nonanol, 3,4-dimethyl-2-nonanol, 3,5-dimethyl-2-nonanol, 3,6-dimethyl-2-nonanol, 3,7-dimethyl-2-nonanol, 3,8-dimethyl-2-nonanol, 4,4-dimethyl-2-nonanol, 4,5-dimethyl-2-nonanol, 4,6-dimethyl-2-nonanol, 4,7-dimethyl-2-nonanol, 4,8-dimethyl-2-nonanol, 5,5-dimethyl-2-nonanol, 5,6-dimethyl-2-nonanol, 5,7-dimethyl-2-nonanol, 5,8-dimethyl-2-nonanol, 6,6-dimethyl-2-nonanol, 6,7-dimethyl-2-nonanol, 6,8-dimethyl-2-nonanol, 7,7-dimethyl-2-nonanol, 7,8-dimethyl-2-nonanol, 8,8-dimethyl-2-nonanol, 3,5,5-trimethyl-1-hesanol, and the like. Even if optical isomers are present, the individual isomer or the mixture thereof may be used.

As liner or branched unsaturated alcohols among the linear, branched or cyclic alcohols having 6 to 18 carbon atoms, which may have an unsaturated bond, an ether group, an aromatic ring and/or an fused ring derived from an aromatic ring in C of the formula (1), there may be exemplified, but not particularly limited to, 2-hexen-1-ol, 3-hexen-1-ol, 4-hepten-2-ol, 3-octen-2-ol, 1-octen-3-ol, 5-nonen-2-ol, 5-decen-2-ol, 9-decen-1-ol, 5-undecen-2-ol, 10-undecen-1-ol, 5-tetradecen-2-ol, 3-methyl-4-hexen-2-ol, 4-methyl-4-hexen-2-ol, 5-methyl-4-hexen-2-ol, 3-methyl-4-hepten-2-ol, 4-methyl-4-hepten-2-ol, 5-methyl-4-hepten-2-ol, 6-methyl-4-hepten-2-ol, 3-methyl-3-octen-2-ol, 1,4-methyl-3-octen-2-ol, 5-methyl-3-octen-2-ol, 6-methyl-3-octen-2-ol, 7-methyl-3-octen-2-ol, 3-methyl-5-nonen-2-ol, 4-methyl-5-nonen-2-ol, 5-methyl-5-nonen-2-ol, 6-methyl-5-nonen-2-ol, 7-methyl-5-nonen-2-ol, 8-methyl-5-nonen-2-ol, 3-methyl-5-decen-2-ol, 4-methyl-5-decen-2-ol, 4-methyl-3-decen-5-ol, 5-methyl-5-decen-2-ol, 6-methyl-5-decen-2-ol, 7-methyl-5-decen-2-ol, 8-methyl-5-decen-2-ol, 9-methyl-5-decen-2-ol, 3,4-dimethyl-3-penten-2-ol, 3,3-dimethyl-4-hexen-2-ol, 3,4-dimethyl-4-hexen-2-ol, 3,5-dimethyl-4-hexen-2-ol, 4,5-dimethyl-4-hexen-2-ol, 3,3-dimethyl-4-hepten-2-ol, 3,4-dimethyl-4-hepten-2-ol, 3,5-dimethyl-4-hepten-2-ol, 3,6-dimethyl-4-hepten-2-ol, 4,5-dimethyl-4-hepten-2-ol, 4,6-dimethyl-4-hepten-2-ol, 5,6-dimethyl-4-hepten-2-ol, 6,6-dimethyl-4-hepten-2-ol, 3,4-dimethyl-3-octen-2-ol, 3,5-dimethyl-3-octen-2-ol, 3,6-dimethyl-3-octen-2-ol, 3,7-dimethyl-3-octen-2-ol, 4,5-dimethyl-3-octen-2-ol, 4,6-dimethyl-3-octen-2-ol, 4,7-dimethyl-3-octen-2-ol, 5,5-dimethyl-3-octen-2-ol, 5,6-dimethyl-3-octen-2-ol, 5,7-dimethyl-3-octen-2-ol, 6,6-dimethyl-3-octen-2-ol, 6,7-dimethyl-3-octen-2-ol, 7,7-dimethyl-3-octen-2-ol, 3,3-dimethyl-5-nonen-2-ol, 3,4-dimethyl-5-nonen-2-ol, 3,5-dimethyl-5-nonen-2-ol, 3,6-dimethyl-5-nonen-2-ol, 3,7-dimethyl-5-nonen-2-ol, 3,8-dimethyl-5-nonen-2-ol, 4,4-dimethyl-5-nonen-2-ol, 4,5-dimethyl-5-nonen-2-ol, 4,6-dimethyl-5-nonen-2-ol, 4,7-dimethyl-5-nonen-2-ol, 4,8-dimethyl-5-nonen-2-ol, 5,6-dimethyl-5-nonen-2-ol, 5,7-dimethyl-5-nonen-2-ol, 5,8-dimethyl-5-nonen-2-ol, 6,7-dimethyl-5-nonen-2-ol, 6,8-dimethyl-5-nonen-2-ol, 7,7-dimethyl-5-nonen-2-ol, 7,8-dimethyl-5-nonen-2-ol, 8,8-dimethyl-5-nonen-2-ol, 2,6-nonadien-1-ol, linalool, ethyllinalool, dihydrolinalool, geraniol, nerol, citronellol, rhodinol, myrcenol, lavandulol, isodihydrolavandulol, dihydromyrcenol, allocimenol, and the like. Even if geometrical or optical isomers are present, the individual isomer or the mixture thereof may be used.

As ether group-containing liner or branched saturated alcohols among the linear, branched or cyclic alcohols having 6 to 18 carbon atoms, which may have an unsaturated bond, an ether group, an aromatic ring and/or an fused ring derived from an aromatic ring in C of the formula (1), there may be exemplified, but not particularly limited to, 3-methoxy-3-methyl-butanol, 3-methoxyhexanol, 3-methoxyheptanol, 3-methoxyoctanol, 3-methoxynonanol, 3-methoxydecanol, 3-methoxytridecanol, 2-methyl-3-methoxyhexanol, 3-methyl-3-methoxyhexanol, 4-methyl-3-methoxyhexanol, 5-methyl-3-methoxyhexanol, 2-methyl-3-methoxyheptanol, 3-methyl-3-methoxyheptanol, 4-methyl-3-methoxyheptanol, 5-methyl-3-methoxyheptanol, 6-methyl-3-methoxyheptanol, 2-methyl-3-methoxyoctanol, 3-methyl-3-methoxyoctanol, 4-methyl-3-methoxyoctanol, 5-methyl-3-methoxyoctanol, 6-methyl-3-methoxyoctanol, 7-methyl-3-methoxyoctanol, 2-methyl-3-methoxynonanol, 3-methyl-3-methoxynonanol, 4-methyl-3-methoxynonanol, 5-methyl-3-methoxynonanol, 6-methyl-3-methoxynonanol, 7-methyl-3-methoxynonanol, 8-methyl-3-methoxynonanol, 2,3-dimethyl-3-methoxypentanol, 2,4-dimethyl-3-methoxypentanol, 2,2-dimethyl-3-methoxypentanol, 3,4-dimethyl-3-methoxypentanol, 4,4-dimethyl-3-methoxypentanol, 2,2-dimethyl-3-methoxyhexanol, 2,3-dimethyl-3-methoxyhexanol, 2,4-dimethyl-3-methoxyhexanol, 2,5-dimethyl-3-methoxyhexanol, 3,4-dimethyl-3-methoxyhexanol, 3,5-dimethyl-3-methoxyhexanol, 4,4-dimethyl-3-methoxyhexanol, 4,5-dimethyl-3-methoxyhexanol, 5,5-dimethyl-3-methoxyhexanol, 2,2-dimethyl-3-methoxyheptanol, 2,3-dimethyl-3-methoxyheptanol, 2,4-dimethyl-3-methoxyheptanol, 2,5-dimethyl-3-methoxyheptanol, 2,6-dimethyl-3-methoxyheptanol, 3,4-dimethyl-3-methoxyheptanol, 3,5-dimethyl-3-methoxyheptanol, 3,6-dimethyl-3-methoxyheptanol, 4,4-dimethyl-3-methoxyheptanol, 4,5-dimethyl-3-methoxyheptanol, 4,6-dimethyl-3-methoxyheptanol, 5,5-dimethyl-3-methoxyheptanol, 5,6-dimethyl-3-methoxyheptanol, 6,6-dimethyl-3-methoxyheptanol, 2,2-dimethyl-3-methoxyoctanol, 2,3-dimethyl-3-methoxyoctanol, 2,4-dimethyl-3-methoxyoctanol, 2,5-dimethyl-3-methoxyoctanol, 2,6-dimethyl-3-methoxyoctanol, 2,7-dimethyl-3-methoxyoctanol, 3,4-dimethyl-3-methoxyoctanol, 3,5-dimethyl-3-methoxyoctanol, 3,6-dimethyl-3-methoxyoctanol, 3,7-dimethyl-3-methoxyoctanol, 4,4-dimethyl-3-methoxyoctanol, 4,5-dimethyl-3-methoxyoctanol, 4,6-dimethyl-3-methoxyoctanol, 4,7-dimethyl-3-methoxyoctanol, 5,5-dimethyl-3-methoxyoctanol, 5,6-dimethyl-3-methoxyoctanol, 5,7-dimethyl-3-methoxyoctanol, 6,6-dimethyl-3-methoxyoctanol, 6,7-dimethyl-3-methoxyoctanol, 7,7-dimethyl-3-methoxyoctanol, and the like. Even if optical isomers are present, the individual isomer or the mixture thereof may be used.

As ether group-containing liner or branched unsaturated alcohols having among the linear, branched or cyclic alcohol having 6 to 18 carbon atoms, which may have an unsaturated bond, an ether group, an aromatic ring and/or an fused ring derived from an aromatic ring in C of the formula (1), there may be exemplified, but not particularly limited to, 5-methoxy-2-hexenol, 5-methoxy-2-heptenol, 5-methoxy-2-octenol, 5-methoxy-2-nonenol, 5-methoxy-2-decenol, 5-methoxy-2-tridecenol, 5-methoxy-2-undecenol, 2-methyl-5-methoxy-2-hexenol, 3-methyl-5-methoxy-2-hexenol, 4-methyl-5-methoxy-2-hexenol, 5-methyl-5-methoxy-2-hexenol, 2-methyl-5-methoxy-2-heptenol, 3-methyl-5-methoxy-2-heptenol, 4-methyl-5-methoxy-2-heptenol, 5-methyl-5-methoxy-2-heptenol, 6-methyl-5-methoxy-2-heptenol, 2-methyl-5-methoxy-2-octenol, 3-methyl-5-methoxy-2-octenol, 4-methyl-5-methoxy-2-octenol, 5-methyl-5-methoxy-2-octenol, 6-methyl-5-methoxy-2-octenol, 7-methyl-5-methoxy-2-octenol, 2-methyl-5-methoxy-2-nonenol, 3-methyl-5-methoxy-2-nonenol, 4-methyl-5-methoxy-2-nonenol, 5-methyl-5-methoxy-2-nonenol, 6-methyl-5-methoxy-2-nonenol, 7-methyl-5-methoxy-2-nonenol, 8-methyl-5-methoxy-2-nonenol, 2-methyl-5-methoxy-2-decenol, 3-methyl-5-methoxy-2-decenol, 4-methyl-5-methoxy-2-decenol, 5-methyl-5-methoxy-2-decenol, 6-methyl-5-methoxy-2-decenol, 7-methyl-5-methoxy-2-decenol, 8-methyl-5-methoxy-2-decenol, 9-methyl-5-methoxy-2-decenol, 2,3-dimethyl-4-methoxy-2-pentenol, 2,4-dimethyl-4-methoxy-2-pentenol, 3,4-dimethyl-4-methoxy-2-pentenol, 2,3-dimethyl-5-methoxy-2-hexenol, 2,4-dimethyl-5-methoxy-2-hexenol, 2,5-dimethyl-5-methoxy-2-hexenol, 3,4-dimethyl-5-methoxy-2-hexenol, 3,5-dimethyl-5-methoxy-2-hexenol, 4,4-dimethyl-5-methoxy-2-hexenol, 4,5-dimethyl-5-methoxy-2-hexenol, 2,3-dimethyl-5-methoxy-2-heptenol, 2,4-dimethyl-5-methoxy-2-heptenol, 2,5-dimethyl-5-methoxy-2-heptenol, 2,6-dimethyl-5-methoxy-2-heptenol, 3,4-dimethyl-5-methoxy-2-heptenol, 3,5-dimethyl-5-methoxy-2-heptenol, 3,6-dimethyl-5-methoxy-2-heptenol, 4,4-dimethyl-5-methoxy-2-heptenol, 4,5-dimethyl-5-methoxy-2-heptenol, 4,6-dimethyl-5-methoxy-2-heptenol, 5,6-dimethyl-5-methoxy-2-heptenol, 6,6-dimethyl-5-methoxy- 2-heptenol, 2,3-dimethyl-5-methoxy-2-octenol, 2,4-dimethyl-5-methoxy-2-octenol, 2,5-dimethyl-5-methoxy-2-octenol, 2,6-dimethyl-5-methoxy-2-octenol, 2,7-dimethyl-5-methoxy-2-octenol, 3,4-dimethyl-5-methoxy-2-octenol, 3,5-dimethyl-5-methoxy-2-octenol, 3,6-dimethyl-5-methoxy-2-octenol, 3,7-dimethyl-5-methoxy-2-octenol, 4,4-dimethyl-5-methoxy-2-octenol, 4,5-dimethyl-5-methoxy-2-octenol, 4,6-dimethyl-5-methoxy-2-octenol, 4,7-dimethyl-5-methoxy-2-octenol, 5,6-dimethyl-5-methoxy-2-octenol, 5,7-dimethyl-5-methoxy-2-octenol, 6,6-dimethyl-5-methoxy-2-octenol, 6,7-dimethyl-5-methoxy-2-octenol, 7,7-dimethyl-5-methoxy-2-octenol, 2,3-dimethyl-5-methoxy-2-nonenol, 2,4-dimethyl-5-methoxy-2-nonenol, 2,5-dimethyl-5-methoxy-2-nonenol, 2,6-dimethyl-5-methoxy-2-nonenol, 2,7-dimethyl-5-methoxy-2-nonenol, 2,8-dimethyl-5-methoxy-2-nonenol, 3,4-dimethyl-5-methoxy-2-nonenol, 3,5-dimethyl-5-methoxy-2-nonenol, 3,6-dimethyl-5-methoxy-2-nonenol, 3,7-dimethyl-5-methoxy-2-nonenol, 3,8-dimethyl-5-methoxy-2-nonenol, 4,4-dimethyl-5-methoxy-2-nonenol, 4,5-dimethyl-5-methoxy-2-nonenol, 4,6-dimethyl-5-methoxy-2-nonenol, 4,7-dimethyl-5-methoxy-2-nonenol, 4,8-dimethyl-5-methoxy-2-nonenol, 5,6-dimethyl-5-methoxy-2-nonenol, 5,7-dimethyl-5-methoxy-2-nonenol, 5,8-dimethyl-5-methoxy-2-nonenol, 6,6-dimethyl-5-methoxy-2-nonenol, 6,7-dimethyl-5-methoxy-2-nonenol, 6,8-dimethyl-5-methoxy-2-nonenol, 7,7-dimethyl-5-methoxy-2-nonenol, 7,8-dimethyl-5-methoxy-2-nonenol, 8,8-dimethyl-5-methoxy-2-nonenol, 5-methoxy-3-heptenol, 5-methoxy-3-octenol, 5-methoxy-3-nonenol, 5-methoxy-3-decenol, 5-methoxy-3-undecenol, 2-methyl-5-methoxy-3-hexenol, 3-methyl-5-methoxy-3-hexenol, 4-methyl-5-methoxy-3-hexenol, 5-methyl-5-methoxy-3-hexenol, 2-methyl-5-methoxy-3-heptenol, 3-methyl-5-methoxy-3-heptenol, 4-methyl-5-methoxy-3-heptenol, 5-methyl-5-methoxy-3-heptenol, 6-methyl-5-methoxy-3-heptenol, 2-methyl-5-methoxy-3-octenol, 3-methyl-5-methoxy-3-octenol, 4-methyl-5-methoxy-3-octenol, 5-methyl-5-methoxy-3-octenol, 6-methyl-5-methoxy-3-octenol, 7-methyl-5-methoxy-3-octenol, 2-methyl-5-methoxy-3-nonenol, 3-methyl-5-methoxy-3-nonenol, 4-methyl-5-methoxy-3-nonenol, 5-methyl-5-methoxy-3-nonenol, 6-methyl-5-methoxy-3-nonenol, 7-methyl-5-methoxy-3-nonenol, 8-methyl-5-methoxy-3-nonenol, 2-methyl-5-methoxy-3-decenol, 3-methyl-5-methoxy-3-decenol, 4-methyl-5-methoxy-3-decenol, 5-methyl-5-methoxy-3-decenol, 6-methyl-5-methoxy-3-decenol, 7-methyl-5-methoxy-3-decenol, 8-methyl-5-methoxy-3-decenol, 9-methyl-5-methoxy-3-decenol and the like. Even if geometrical or optical isomers are present, the individual isomer or the mixture thereof may be used.

As alcohols which may have an alicyclic structure among the linear, branched or cyclic alcohols having 6 to 18 carbon atoms, which may have an unsaturated bond, an ether group, an aromatic ring and/or an fused ring derived from an aromatic ring in C of the formula (1), there may be exemplified, but not particularly limited to, cyclohexanol, 2-methylcyclopentanol, 3-methylcyclopentanol, 2-methyl-1-cyclopentenol, 3-methyl-1-cyclopentenol, 4-methyl-1-cyclopentenol, 5-methyl-1-cyclopentenol, 2-methyl-2-cyclopentenol, 3-methyl-2-cyclopentenol, 4-methyl-2-cyclopentenol, 5-methyl-2-cyclopentenol, 2-methyl-3-cyclopentenol, 3-methyl-3-cyclopentenol, 4-methyl-3-cyclopentenol, 5-methyl-3-cyclopentenol, 2,2-dimethylcyclopentanol, 2,3-dimethylcyclopentanol, 2,4-dimethylcyclopentanol, 2,5-dimethylcyclopentanol, 3,3-dimethylcyclopentanol, 3,4-dimethylcyclopentanol, 2,4-dimethyl-3-cyclohexenylmethanol, 2-cyclopentylethan-1-ol, 2-(2,2,3-trimethyl-3-cyclopentenyl)-ethan-1-ol, 1-cyclohexenol, 2-cyclohexenol, 3-cyclohexenol, 2-methyl-1-cyclohexenol, 3-methyl-1-cyclohexenol, 4-methyl-1-cyclohexenol, 4-isopropyl-1-cyclohexanol, 4-isopropyl-1-cyclohexylmethanol, 1-(4-isopropyl-1-cyclohexyl)ethanol, 5-methyl-1-cyclohexenol, 6-methyl-1-cyclohexenol, 2-methyl-2-cyclohexenol, 3-methyl-2-cyclohexenol, 4-methyl-2-cyclohexenol, 5-methyl-2-cyclohexenol, 6-methyl-2-cyclohexenol, 2-methyl-3-cyclohexenol, 3-methyl-3-cyclohexenol, 4-methyl-3-cyclohexenol, 5-methyl-3-cyclohexenol, 6-methyl-3-cyclohexenol, 2,2,6-trimethylcyclohexyl alcohol, 2,2,6-trimethyl-6-cyclohexenol, 2,2,6-trimethyl-5-cyclohexenol, 2,2,6-trimethyl-4-cyclohexenol, 2,2-dimethyl-6-exomethyl-6-cyclohexenol, 4-tert-butylcyclohexanol, 2-tert-butylcyclohexanol, terpineol, borneol, nopol, ambrinol, and the like. Even if geometrical or optical isomers are present, the individual isomer or the mixture thereof may be used.

As alcohols which may have an aromatic ring among the linear, branched or cyclic alcohols having 6 to 18 carbon atoms, which may have an unsaturated bond, an ether group, an aromatic ring and/or an fused ring derived from an aromatic ring in C of the formula (1), there may be exemplified, but not particularly limited to, benzyl alcohol, styrallyl alcohol, hydroquinone, furfuryl alcohol, 4-hydroxystyrallyl alcohol, vanillyl alcohol, cuminic alcohol, 2-methylbenzyl alcohol, 3-methylbenzyl alcohol, 4-methylbenzyl alcohol, α-dimethylbenzyl alcohol, α-phenethyl alcohol, β-phenethyl alcohol, cinnamic alcohol, 4-hydroxy-3-methoxystyrallyl alcohol, anisyl alcohol, catechol, 5-methylfurfuryl alcohol, 2-pyridinylethanol and the like. Even if geometrical or optical isomers are present, the individual isomer or the mixture thereof may be used.

Furthermore, as the alcohols which may have a fused ring derived from an aromatic ring among the linear, branched or cyclic alcohols with 6 to 18 carbon atoms which may have an unsaturated bond and an ether group, an aromatic ring and/or a fused ring derived from an aromatic ring in C of the formula (1), there may be exemplified, but not particularly limited to, 6-methyl-1-indanol, alpha tetralol, 1-naphthyl methanol, 2-naphthyl methanol, piperonyl alcohol, 3-chromon alcohol, 2-benzofurfuryl alcohol and the like. Even if geometrical or optical isomers are present, the individual isomer or the mixture thereof may be used.

Compounds of the invention may be synthesized according to a technique that is well known in the art. Although not specifically limited, they can be obtained by an one-step or preferably two-step condensation of a dicarboxylic acid such as oxalic acid, malonic acid, succinic acid, glutaric acid, adipic acid, fumaric acid and maleic acid with alcohols which can form the alcohol residue of the formula (1) in the presence of an appropriate condensation agent. A desired diester may be obtained as follows. That is, an acid anhydride of the aforementioned dicarboxylic acid is reacted with the aforementioned alcohols in the absence or presence of an acid or base catalyst to synthesize a half ester, and then the half ester is condensed with an alcohol in the presence of a condensation agent, or the carboxylic acid residue of the half ester is converted into an activated ester or acid halide to react with the alcohol. It is also possible to use a lipase enzyme as an esterifying agent.

As the condensation agent, there may be exemplified dicyclohexyl carbodiimide, diisopropyl carbodiimide, 1-ethyl-3-(3-dimethylaminopropyl)carbodiimide, and 2-methyl-6-nitrobenzoic acid anhydride, and the like. Further, as the acid catalyst, there may be exemplified sulfuric acid, hydrochloric acid, phosphoric acid, sodium hydrogen sulfate, methane sulfonic acid, para-toluene sulfonic acid, and the like. As the base catalyst, there may be exemplified sodium carbonate, potassium carbonate, sodium methoxide, potassium butoxide, sodium acetate, pyridine, dimethylamino pyridine, triethylamine, and the like. In addition, as the lipase enzyme, there may be exemplified Lipase PS (trade name, manufactured by AMANO Corporation), Lipase AY (trade name, manufactured by AMANO Corporation), Novozyme 435 (trade name, manufactured by Novozymes), Novozyme 525 (trade name, manufactured by Novozymes), and the like.

The diester compounds of dicarboxylic acid according to the invention represented by the formula (1), which is obtained as above, have a long-lasting cooling sensation effect even if they are used alone or as a mixture of two or more. Therefore, it can be utilized as a cooling sensation agent or a sensory stimulation agent either alone or as a mixture of two or more.

Although the diester compound of dicarboxylic acid of the invention, that is obtained as above, is needed to alter an amount compounded or an application method according to types and purposes of use of the product, an amount for a flavor or fragrance agent composition, generally, is preferably 0.0001 to 90% by mass to the total mass of the composition. On the other hand, an amount for a beverage, a food product, a perfume or cosmetic product, a toiletry product, daily utensil products or groceries, a fiber, a fiber product, clothes, clothing or a medicine or the like is $1 \times 10^{-7}$ to 20% by mass, preferably 0.0001 to 20% by mass, and more preferably 0.001 to 5% by mass to the total mass of the composition.

The cooling sensation agent composition of the invention contains at least one of the dicarboxylic esters described above. That is, the cooling sensation agent composition of the invention may comprise one of the dicarboxylic esters or two or more of the dicarboxylic esters. Further, the dicarboxylic ester compound of the invention may be used as it is for a cooling sensation agent composition or used as a solution in alcohol, propylene glycol, benzyl benzoate and the like or as an emulsion admixed with an emulsifying agent for a cooling sensation agent composition.

Furthermore, a cooling sensation agent composition having increased cooling sensation strength may be obtained using the dicarboxylic ester compounds of the invention together with at least one selected from cooling sensation substances that are not included in the ester compounds of the invention.

As the cooling substances which are not included in the dicarboxylic ester compounds of the invention, there may be exemplified menthol, menthone, camphor, pulegol, isopulegol, cineole, mint oil, peppermint oil, spearmint oil, eucalyptus oil, 3-(l-menthoxy)propane-1,2-diol, N-alkyl-p-menthane-3-carboxamide, 3-l-menthoxy-2-methylpropane-1,2-diol, p-menthane-3,8-diol, 2-l-menthoxyethan-1-ol, 3-l-menthoxypropan-1-ol, 4-l-menthoxybutan-1-ol (menthyl 3-hydroxybutanoate), menthyl lactate, menthone glycerin ketal, N-methyl-2,2-isopropylmethyl-3-methylbutane amide, menthyl glyoxylate and the like. These can be used alone or as an appropriate mixture of two or more.

The dicarboxylic ester compounds of the invention and the cooling sensation substances which are not included in the dicarboxylic ester compounds of the invention may be used at any ratio within a range in which the effect of the invention is not impaired. However, the ratio is preferably, in terms of mass ratio of the dicarboxylic ester compounds of the invention to the cooling substance which is not included in the compounds, in the range of 1:99 to 70:30.

Further, in the invention, since the aforementioned cooling sensation agent composition of the invention has a strong and long-lasting cooling sensation effect, a sensory stimulation agent composition having a cooling sensation effect can be produced by containing this cooling sensation agent composition. In addition, the sensory stimulation agent composition of the invention is a composition having an action to stimulate senses. The sense-stimulating action includes both cooling action and warming action, and thus in the present invention, the sensory stimulation agent composition is a concept including both the cooling sensation agent composition and warming and pungent agent composition.

In preparing a sensory stimulation agent composition, the field and method of application of the cooling sensation agent composition should be altered properly according to the kind and application purpose of the product, and the cooling sensation agent composition is normally used in a compounding amount of 0.0001 to 20% by mass, particularly preferably 0.001 to 5% by mass, in the entire sensory stimulation agent composition.

The sensory stimulation agent composition may be prepared by using a warming and pungent substance in combination with the cooling sensation agent composition of the invention. Examples of the warming substances include vanillyl ethyl ether, vanillyl propyl ether, vanillin propylene glycol acetal, ethylvanillin propylene glycol acetal, capsaicin, gingerol, vanillyl butyl ether, 4-(l-menthoxy-methyl)-2-(3'-methoxy-4'-hydroxyphenyl)-1,3-dioxolane, pepper oil, pepper oleoresin, ginger oleoresin, nonanoic vanillylamide, jamboo oleoresin, Zanthoxylum Piperitum Peel Extract, sanshool-I, sanshool-II, sanshoamide, black pepper extract, chavicine, piperine, spilanthol and the like. These substances may be used alone or as a mixture of two or more.

If the cooling action is desirable, the compounding ratio of the warming and pungent substance to the cooling sensation substance is in the range where the warming action by the warming substance is not distinctively observed by compounding of the warming substance, and thus, the compounding amount of the warming and pungent substance is normally 0.001 to 0.95 part, preferably 0.01 to 0.5 part, with respect to the total amount of the cooling sensation agent composition. In this case, the cooling action is further improved and strengthened by addition of the warming and pungent substance to the cooling sensation agent composition in the amount described above in the sensory stimulation agent composition of the present invention. Alternatively if the warming action is desirable, the cooling sensation agent composition is added to a warming composition in an amount not distinctively showing the cooling action by the cooling sensation agent composition compounded, and the compounding amount is normally 0.001 to 0.95 part, preferably 0.01 to 0.5 part, with respect to the total amount of the warming and pungent agent.

The cooling sensation agent composition and the sensory stimulation agent composition of the invention can be compounded with a flavor or fragrance composition. When the cooling sensation agent composition or the sensory stimulation agent composition is compounded with the flavor or fragrance composition, the compounding amount thereof should be altered properly according to the scope, application method, kind and purpose of use of the flavor or fragrance composition, but is preferred in the range of normally 0.0001 to 90% by mass with respect to the total amount of the flavor or fragrance composition. In addition, the cooling sensation agent composition and the sensory stimulation agent composition of the present invention can be compounded with a flavor or fragrance composition, a beverage, a food product, a perfume or cosmetic product, a toiletry product, daily utensil products and groceries, a medicine and others. when the cooling sensation agent composition or the sensory stimulation agent composition is compounded in such a product, the compounding amount thereof may vary according to the kind of the product to be compounded, but is preferably $1 \times 10^{-7}$ to 20% by mass, more preferably 0.0001 to 20% by mass, particularly preferably 0.001 to 5% by mass, with respect to the total amount of the product composition. The products can be applied directly onto a skin or a scalp, administered into an oral cavity, or applied to fibers, fiber products, clothes or clothing. Especially when the cooling sensation agent composition of the present invention is used, long-lasting cooling feeling is provided to the skin, scalp, or oral cavity since the cooling sensation agent composition has a strong, long-lasting cool action. Alternatively, the cooling sensation agent composition or the sensory stimulation agent composition can be used in processing of a fiber, a fiber product, clothes, clothing, resin and the like. The compounding amount thereof should be altered properly according to the application scope, purpose of use, kind and application method of the product and others, but is normally 0.0001 to 20% by mass, particularly preferably 0.001 to 5% by mass in concentration.

For example, the cooling sensation agent composition or the sensory stimulation agent composition of the present invention may be directly sprayed on, adsorbed in or permeated to the fibers, resins, cloth materials, clothes or clothing, or may be used for modification or processing of the surface or internal region of the fiber or the resin surface by using a suitable solvent, a dispersion medium or microcapsules. The compounding amount thereof is preferably 0.0001 to 100% by mass, particularly preferably 0.001 to 100% by mass with respect to the total amount of the fragrance composition, the processing agent composition or the internal composition in the microcapsule.

The fiber material to be processed is not particularly limited, and examples thereof include natural fibers such as cellulose, cotton, hemp, silk and wool; regenerated fibers such as rayon, cupra, polynosic, Tencel (trade name), and Lyocell (trade name); semi-synthetic fibers such as acetates; chemically synthetic fibers such as nylon, polyester, and acrylic; and the like. These fibers may be used alone or as a fiber obtained by mixed spinning or mixed weaving in which two kind or more of fibers are used. The forms of the fibers include yarn, woven and knitted fabrics, nonwoven fabric, paper and the like, but are not particularly limited thereto.

Wall materials of the microcapsule is preferably an organic material, and examples thereof include polystyrene, ethylcellulose, polyamide, polyacrylic acid, melamine, silicone resin and the like, but are not limited thereto.

The average particle diameter of the microcapsule is not particularly limited, but preferably 20 µm or less, more preferably 10 µm or less, still more preferably 5 µm or less, because of dispersibility when used as a processing solution, prevention of breakage of microcapsules under pressure during processing as they are adhered to fibers, and prevention of hardening in texture.

The method for producing the microcapsule is not particularly limited and includes known methods, for example those described in JP-A Nos. 62-1452, 62-45680, 62-149334, 62-225241, 63-115718, 63-217196, and 2-258052, JP Patent No. 3,059,558 and others.

The adhesion methods of the microcapsule-dispersed processing solution to fibers or resins include, for example, a pad drying method, a spraying method, a printing method, a coating method and the like, but are not particularly limited thereto.

Cool feeling may be given to fiber products, clothes and the like by compounding the cooling sensation agent composition or the sensory stimulation agent composition of the invention with a detergent, a fabric softener or the like in advance, and then adhering the cooling sensation agent composition or the sensory stimulation agent composition of the invention onto the fiber products, clothes or the like at the time of washing or rinsing. The compounding amount of these compositions in a detergent, a fabric softener or the like is not particularly limited, but should be an amount of a level where cool feeling is recognized at the time of touching to or wearing a fiber product, clothes or clothing after washing and drying. The amount is normally 0.0000001 to 10% by mass, preferably 0.000001 to 5% by mass with respect to the total composition of a detergent, a fabric softener or the like.

The cooling sensation agent composition and the sensory stimulation agent composition of the present invention may be compounded directly with various products such as flavor or fragrance compositions, beverage, food products, perfume or cosmetic products, toiletry products, daily utensil products and groceries, fibers, fiber products, clothes, clothing and medicines. In addition, the cooling sensation agent composition and the sensory stimulation agent composition may be first compounded with a flavor or fragrance composition to give a flavor or fragrance composition containing the cooling sensation agent composition or the sensory stimulation agent composition, and then, the cooling sensation agent composition, the sensory stimulation agent composition, or the flavor or fragrance composition containing the cooling sensation agent composition or the sensory stimulation agent composition may be compounded with the product.

Examples of the flavor or fragrance components contained in combination with the cooling sensation agent composition and the sensory stimulation agent composition of the present invention include various synthesis aromachemicals, natural essential oils, synthetic essential oils, citrus oils, animal aromachemicals and the like, and there also may be used various kinds of flavor or fragrance components such as those described, for example, in "Collection of Well-known Prior Arts (Flavor or Fragrances) 1st part", Japanese Patent Office, Jan. 29, 1999. Typical examples thereof include α-pinene, limonene, cis-3-hexenol, phenylethyl alcohol, styralyl acetate, eugenol, Oxyde de rose, linalool, benzaldehyde, l-muscone (Takasago International Corporation), Musk T (Takasago International Corporation), Thesaron (Takasago International Corporation) and the like.

The content of the cooling sensation agent composition or the sensory stimulation agent composition in the flavor or fragrance composition containing the cooling sensation agent composition or the sensory stimulation agent composition of the invention may be adjusted properly according to the kind and purpose of use of the flavor or fragrance and other components to be mixed. For example, in the case of a fragrance composition, the content of the cooling sensation agent composition is normally 0.0001 to 50% by mass, preferably 0.001 to 50% by mass, and more preferably 0.01 to 20% by mass with respect to the total mass of the fragrance composition.

Alternatively, in the case of a flavor composition, the content of the cooling sensation agent composition is preferably 0.0001 to 50% by mass and more preferably 0.001 to 30% by mass with respect to the total mass of the flavor composition.

The cooling sensation agent composition and the sensory stimulation agent composition of the present invention may contain, as needed, one or more odorant-retaining agents commonly used in flavor or fragrance compositions. Example of the odorant-retaining agents used include ethylene glycol, propylene glycol, dipropylene glycol, glycerol, hexyl glycol, benzyl benzoate, triethyl citrate, diethyl phthalate, hercolin, medium-chain fatty acid triglycerides, medium-chain fatty acid diglycerides and the like. These compounds may be contained alone or as a mixture of two or more.

The cooling sensation agent composition and the sensory stimulation agent composition of the present invention can be used for providing cooling action to various products, as described above, by using the cooling sensation agent composition alone or as a flavor or fragrance containing the cooling sensation agent composition. The products to which the cooling action can be provided using the cooling sensation agent composition itself or the flavor or fragrance composition containing the cooling sensation agent composition of the present invention include beverages, food products, perfume or cosmetic products, daily utensil products and groceries, toiletry products, fibers, fiber products, clothes, clothing, medicines and the like, as described above.

Unlimited examples of the beverages and food products of the invention capable of giving the cooling sensation or the like by the cooling sensation agent composition, the sensory stimulant composition or the flavor composition containing these composition include beverages such as fruit beverages, fruit spirits, milk-based drinks, carbonated drinks, soft drinks and health and nutrient drinks; frozen deserts such as ice creams, sherbets and popsicles; deserts such as jelly and puddings; confectionary such as cakes, cookies, chocolates and chewing gums; Japanese sweets such as bean-jam buns, thick jellied sweet made of azuki bean paste and thick jellied sweet made of powdered rice paste; jams; candies; breads; tea drinks and other favorite drinks such as green tea, oolong tea, black tea, persimmon leaf tea, chamomile tea, sasa veitchii tea, mulberry leaf tea, Houttuynia cordata tea, puaar tea, mate tea, rooibos tea, gymnema tea, guava tea, coffee and cocoa; soups such as Japanese style soups, Western style soups and Chinese style soups; flavored seasonings; various instant drinks and foods; various snacks; and oral products such as toothpaste, tooth powder, oral wash, mouth wash, throat lozenge, and chewing gums.

Examples of the perfume or cosmetic products, toiletry products or daily utensil products and groceries of the invention capable of giving the cooling sensation or the like by the cooling sensation agent composition, the sensory stimulant composition or the fragrance composition containing these composition include perfume or cosmetic products, skin-care cosmetics, make-up cosmetics, hair cosmetics, anti-sunburn cosmetics, medicinal cosmetics, hair-care products, soaps, body lotions, bath utensils, detergents, soft finishing agents, cleaning agents, kitchen detergents, breaching agents, aerosol agents, deodorant-aromatics, repellents, and other groceries.

More specifically, the examples include:

perfume, Eau de Parfum, Eau de Toilette, and Eau de Cologne as the perfume or cosmetic products;

face washing cream, vanishing cream, cleansing cream, cold cream, massage cream, milky lotion, skin lotion, beauty wash, beauty pack, and make-up remover as the skin-care cosmetics;

foundation, face powder, pressed powder, talcum powder, rouge, lip stick, lip cream, cheek rouge, eye liner, mascara, eye shadow, eyebrow-color, eye pack, nail enamel, and enamel remover as the make-up cosmetics; and pomade, brilliantine, set lotion, hair stick, hair solid, hair oil, hair treatment, hair cream, hair tonic, hair liquid, hair spray, bandlin, hair-growing agent, and hair dye as the hair cosmetics.

Examples of the anti-sunburn cosmetics include suntan products and sunscreen products;

examples of the medicinal cosmetics include antiperspirant, after-shaving lotion and gel, permanent wave agent, medicinal soap, medicinal shampoo, and medicinal skin-care cosmetics.

Examples of the hair-care products include shampoo, rinse, rinse-in-shampoo, hair conditioner, hair treatment, and hair pack;

examples of the soaps include toilet soap, bath soap, perfume soap, clear soap, and synthetic soap;

examples of the body cleaners include body soap, body shampoo, and hand soap;

examples of the bath utensils include bath agent such as bath salt, bath tablet and bath liquid, foam bath such as bubble bath, bath oil such as bath perfume and bath capsule, milk bath, bath jelly, and bath cube; and examples of the detergents include heavy detergent for clothes, light detergent for clothes, liquid laundry detergent, laundry soap, compact detergent, and powder detergent.

Examples the soft finishing agents include softener and furniture care;

examples of the cleaning agents include cleanser, house wash, toilet cleaner, bath cleaner, glass cleaner, fungicide, and cleaner for drain pipe;

examples of the kitchen detergents include kitchen soap, kitchen synthetic soap, and dish wash;

examples of the bleaching agents include oxidant bleach such as chlorine bleach and oxygen bleach, reductive bleach such as sulfur containing bleach, and optical bleach;

examples of the aerosol agents include spray type aerosol and powder spray;

examples of the deodorant-aromatics include solid, gel and liquid deodorizer and aromatics; and examples of the groceries include tissue paper and toilet paper.

Examples of the medicines of the invention capable of giving the cooling sensation or the like by the cooling sensation agent composition, the sensory stimulant composition or the flavor or fragrance composition containing these compositions include, but are not limited to, skin external preparations such as poultice and ointment, internal preparations and the like.

When the cooling sensation agent composition, the sensory stimulation agent composition or the flavor or fragrance composition containing these compositions according to the invention is used for providing the aforementioned various products with cooling sensation or the like, they may be added various forms or various methods according to the kind of the products and final product forms such as liquid, solid, powder, gel, mist, aerosol, or the like. For example, they may be added directly to the product; as a liquid dissolved in an alcohol or a polyvalent alcohol such as, propylene glycol, or glycerol; as a solution or dispersion dissolved or dispersed with a natural gum such as gum arabic or tragacanth gum or a surfactant such as nonionic surfactant, e.g. glycerol fatty acid ester or sucrose fatty acid ester, anionic surfactant, cationic surfactant and amphoteric surfactant; as a powder formed with a natural gum such as gum arabic or a shape-imparting agent such as gelatin or dextrin; or as microcapsules treated with an encapsulating agent.

Alternatively, the cooling sensation agent composition, the sensory stimulation agent composition or the flavor or fragrance composition containing these may be stabilized and provided with sustained-release property by inclusion using an inclusion agent such as cyclodextrin.

EXAMPLES

Hereinafter, the invention will be described more specifically with reference to Examples, but it should be understood that the present invention is not restricted by these Examples, and various modifications are possible within the scope of the present invention.

The products obtained in the Synthetic examples and Examples described below were analyzed by using the following instruments and apparatuses:

Nuclear magnetic resonance spectrum: $^1$H-NMR: OXFORD 300 MHz FT-NMR (300 MHz), manufactured by Varian, Inc.

External standard substance: tetramethylsilane

TLC: SILICA GEL 60 F254 (trade name, manufactured by Merck & Co., Inc.)

Synthetic Example 1

Synthesis of l-menthyl-(l-menthoxyethyl)succinic ester(Compound 1)

To a 100 ml autoclave, 10.00 g (63.99 mmol) of l-menthol and 6.40 g (63.96 mmol) of succinic anhydride were added, flushed with nitrogen gas, and then stirred at 110° C. for 8 hours. After cooling to room temperature, 100 ml of hexane was added thereto. The precipitated crystals were filtered and the filtrate, hexane phase was concentrated to obtain 16.61 g of l-menthylsuccinic acid. The yield was >99.9%.

To a 20 ml two-neck flask, 6.00 g (23.42=1) of l-menthyl-succinic acid and 20.0 mg of DMF were added, and 6.00 g (50.43 mmol) of thionyl chloride was added dropwise thereto at room temperature. Upon the completion of the dropwise addition, the mixture was stirred for 2 hours and excess thionyl chloride was removed by distillation under reduced pressure to obtain 6.45 g of l-menthylsuccinic acid chloride. The yield was >99.9%.

To a 50 ml two-neck flask, 1.99 g (9.93 mol) of l-menthoxyethanol, 20 ml of toluene and 2.01 g (19.86 mmol) of triethylamine were added, and 3.00 g (10.92 mmol) of l-menthylsuccinic acid chloride obtained was added dropwise thereto at room temperature. After stirring for 2 hours at room temperature, disappearance of the spot of l-methoxyethanol was confirmed by the thin layer chromatography (TLC) (ethyl acetate:hexane=1:3), and then the reaction was terminated. The reaction solution was diluted with 150 ml of toluene and washed twice with 30 ml of purified water. The organic layer was dried over sodium sulfate and concentrated to obtain 4.84 g of a colorless liquid. Column purification was carried out using 73 g of silica gel and development solution of ethyl acetate:hexane=1:30 to obtain 3.95 g of l-menthyl-(l-menthoxyethyl)succinic ester. The yield was 79.2%.

Physical property of
l-menthyl-(l-menthoxyethyl)succinic ester $^1$H-NMR (CDCl$_3$, 300 MHz): σ 4.70 (1H, ddd, J=10.8, 10.8, 4.5), 4.22 (2H, t, J=6.8), 3.79 (1H, dt, J=11.1, 9.3), 3.52 (1H, dt, J=11.1, 10.8), 3.05 (1H, ddd, J=10.8, 10.8, 4.5), 2.64 (4H, m), 2.22 (1H, m), 2.02 (2H, m), 1.85 (1H, q, J=7.2), 1.84 (1H, m), 1.20-1.33 (4H, m), 0.97-1.07 (4H, m), 0.81-0.93 (12H, m), 0.77 (6H, t, J=8.1)

Synthetic Example 2

Synthesis of l-menthyl-3-(l-menthoxy)-2-(hydroxypropyl)succinic ester(Compound 2)

The synthesis was carried out in the same manner as Synthetic example 1 except for using l-menthylglycerol instead of l-menthoxyethanol to obtain l-menthyl-3-(l-menthoxy)-2-(hydroxyl-propyl)succinic ester. The yield was 75.4%.

Physical property of
l-menthyl-3-(l-menthoxy)-2-hydroxypropyl-succinic ester $^1$H-NMR (CDCl$_3$, 300 MHz): σ 4.69 (1H, ddd, J=10.8, 10.8, 4.5), 3.97-4.23 (2H, m), 3.80 (1H, br), 3.61-3.72 (1H, m), 3.28-3.39 (1H, m), 3.08 (1H, ddd, J=10.8, 10.8, 4.5), 2.64 (4H, m), 1.82-2.17 (4H, m), 1.60-1.68 (4H, m), 1.20-1.46 (6H, m), 0.99-1.11 (4H, m), 0.88-1.06 (12H, m), 0.77 (6H, t, J=6.9)

Synthetic Example 3

Synthesis of l-menthyl-(l-isopulegyl)succinic ester(Compound 3)

The synthesis was carried out in the same manner as Synthetic example 1 except for using l-isopulegol instead of l-menthoxyethanol to obtain l-menthyl-(l-isopulegyl)succinic ester. The yield was 72.4%.

Physical property of l-menthyl-(l-isopulegyl)succinic ester $^1$H-NMR (CDCl$_3$, 300 MHz): σ 4.81 (1H, ddd, J=11.0, 11.0, 4.2), 4.65-4.72 (3H, m), 2.56 (3H, s), 1.81-2.15 (3H, m), 1.65 (3H, s), 1.30-1.60 (6H, m), 0.96-1.11 (6H, m), 0.88-0.94 (9H, m), 0.75 (6H, t, J=6.9)

Synthetic Example 4

Synthesis of l-menthyl-(l-citronellyl)succinic ester(Compound 4)

The synthesis was carried out in the same manner as Synthetic example 1 except for using l-citronellol instead of l-menthoxyethanol to obtain l-menthyl-(l-citronellyl)succinic ester. The yield was 78.6%.

Physical property of l-menthyl-(l-citronellyl)succinic ester $^1$H-NMR (CDCl$_3$, 300 MHz): σ 5.08 (1H, t, J=7.2), 4.69 (1H, ddd, J=10.8, 10.8, 4.2), 4.05-4.17 (2H, m), 2.61 (3H, s), 1.93-2.02 (3H, m), 1.81-1.90 (1H, m), 1.64-1.71 (5H, m), 1.60 (3H, s), 1.29-1.57 (6H, m), 1.07-1.24 (2H, m), 0.88-0.98 (9H, m), 0.75 (3H, J=6.9)

Synthetic Example 5

Synthesis of l-menthyl-(phenylethyl)succinic ester(Compound 5)

The synthesis was carried out in the same manner as Synthetic example 1 except for using phenethyl alcohol instead of l-menthoxyethanol to obtain l-menthyl-(phenylethyl)succinic ester. The yield was 69.0%.

Physical property of l-menthyl-(phenylethyl)succinic ester $^1$H-NMR (CDCl$_3$, 300 MHz): σ 7.20-7.33 (59, m), 4.69 (1H, ddd, J=10.8, 10.8, 4.2), 4.30 (2H, t, J=7.2), 2.94 (2H, t, J=7.2), 2.60 (4H, t, J=7.2), 1.98 (1H, d, J=12.0), 1.85 (1H, t, J=6.9), 1.67 (2H, d, J=12.8), 1.31-1.56 (3H, m), 0.98-1.11 (2H, m), 0.92 (6H, d, J=11.4), 0.75 (3H, d, J=6.6)

Synthetic Example 6

Synthesis of l-menthyl-(phenylethyl)glutaric ester(Compound 6)

To a 200 ml autoclave, 39.00 g (0.25 mol) of l-menthol and 28.5 g (0.25 mol) of glutaric anhydride were added, flushed with nitrogen gas, and stirred at 90° C. for 18 hours. Upon the completion of the reaction, bigelow distillation (Bottom 180 to 195° C., Top 150 to 155° C., 30 Pa) was carried out to obtain 59.64 g of l-menthylglutaric acid. The yield was 88.4%.

Subsequently, to a 200 ml four-neck flask, 10.00 g (36.99 mmol) of l-menthylglutaric acid, 4.52 g (37.00 mmol) of phenethyl alcohol, 100 ml of hexane and 0.50 g (5.0% by weight) of Novozyme 435 were added, and then stirred at 60° C. for 13 hours. After confirming the conversion ratio of 90.9%, the reaction solution was filtered to remove Novozyme 435. The organic layer was concentrated to obtain 14.39 g of a colorless liquid. Column purification was carried out using 300 g of silica gel and development solution of ethyl acetate:hexane=1:30 to obtain 9.51 g of l-menthyl-(phenylethyl)glutaric ester. The yield was 68.7%.

Physical property of l-menthyl-(phenylethyl)glutaric ester $^1$H-NMR (CDCl$_3$, 300 MHz): σ 7.20-7.33 (5H, m), 4.67 (1H, ddd, J=10.8, 10.8, 4.5), 4.30 (2H, t, J=7.2), 2.94 (2H, t, J=7.2), 2.33 (2H, ddd, J=7.5, 7.5, 3.9), 1.81-1.99 (4H, m), 1.68 (2H, m), 1.32-1.59 (3H, m), 1.30-1.40 (2H, m), 1.03-1.08 (2H, m), 0.95 (6H, m), 0.75 (3H, d, J=6.9)

Synthetic Example 7

Synthesis of l-menthyl-(l-citronellyl)glutaric ester(Compound 7)

The synthesis was carried out in the same manner as Synthetic example 6 except for using l-citronellol instead of phenethyl alcohol to obtain l-menthyl-(l-citronellyl)glutaric ester. The yield was 70.0%.

Physical property of l-menthyl-(l-citronellyl)glutaric ester $^1$H-NMR (CDCl$_3$, 300 MHz): σ 5.09 (1H, t, J=7.2), 4.69 (1H, ddd, J=10.8, 10.8, 4.2), 4.11 (2H, m), 2.35 (4H, t, J=7.5), 1.90-2.03 (6H, m), 1.84 (1H, t, J=9.3), 1.64-1.68 (8H, m), 1.60 (3H, d, J=4.2), 1.31-1.55 (4H, m), 1.02-1.24 (2H, m), 0.88-0.98 (9H, m), 0.75 (3H, J=6.9)

Synthetic Example 8

Synthesis of l-menthyl-(l-menthoxyethyl)-glutaric ester(Compound 8)

The synthesis was carried out in the same manner as Synthetic example 6 except for using l-menthoxyethanol instead of phenethyl alcohol to obtain l-menthyl-(l-menthoxyethyl) glutaric ester. The yield was 65.2%.

Physical property of l-menthyl-(l-menthoxyethyl)glutaric ester $^1$H-NMR (CDCl$_3$, 300 MHz): σ 4.68 (1H, ddd, J=10.8, 10.8, 4.5), 4.21 (2H, t, J=6.8), 3.79 (1H, dt, J=11.1, 9.3), 3.52 (1H, dt, J=11.1, 10.8), 3.05 (1H, ddd, J=10.8, 10.8, 4.5), 2.36 (4H, m), 2.18 (1H, m), 2.05 (1H, m), 1.96 (2H, q, J=7.2), 1.84 (1H, m), 1.59-1.69 (10H, m), 1.03-1.50 (5H, m), 0.79-0.93 (12H, m), 0.76 (6H, t, J=6.6)

Test Example 1

Test of a Cooling Towel (Direct Spraying)

Each of Compounds 1 to 8 that were obtained by the above synthetic examples and Mixture 1 which is an equivalent-weight mixture of Compounds 1 to 4, Mixture 2 which is an equivalent-weight mixture of Compounds 5 to 8, Mixture 3 which is an equivalent-weight mixture of Compounds 2, 3 and 8, and dimenthyl glutaric acid and l-menthol as comparative compounds was prepared in 1% ethanol solution. The 1% ethanol solutions were then sprayed respectively by 1 g to different pure cotton hand towels (white plain towel made in Japan, 20 cm×20 cm, degrease-finished). Those which were air-dried for 10 minutes, 3 hours or 24 hours after spraying were sensory evaluated. The sensory evaluation was carried out by touching the cooling towel with the inside of upper parts of arms, and cooling action at that time was determined. Results are shown in Table 1.

Meanwhile, the evaluation was carried out by five panelists having 5 years or longer experience. Compounds 1 to 8 and mixtures 1 to 3 were divided into three groups of A to C, wherein group A consists of Compound 1, mixture 1, Compound 2, dimenthylglutaric acid, and l-menthol; group B consists of mixture 2, Compound 3, Compound 6, dimenthylglutaric acid, and l-menthol; and group C consists of Compound 7, Compound 8, Compound 4, mixture 3, and dimenthylglutaric acid. Then, different 5 kinds of samples were ranked from the strongest to weakest in action respectively by the panelists in each three groups. The results are shown by the total score of the ranking numbers. In other words, smaller total score means to show a better cooling sensation effect.

TABLE 1

Results of comparison concern with lasting properties of cooling effect on treated hand towel at direct spraying

| | | Group A | | | Group B | | | Group C | | |
|---|---|---|---|---|---|---|---|---|---|---|
| | Materials | After 10 min | After 3 hr | After 24 hr | After 10 min | After 3 hr | After 24 hr | After 10 min | After 3 hr | After 24 hr |
| Example 1 | Compound 1 | 18 | 12 | 11 | | | | | | |
| Example 2 | Mixture 1 | 11 | 6 | 5 | | | | | | |
| Example 3 | Compound 2 | 18 | 13 | 13 | | | | | | |
| Example 4 | Mixture 2 | | | | 13 | 7 | 7 | | | |
| Example 5 | Compound 3 | | | | 16 | 10 | 10 | | | |
| Example 6 | Compound 6 | | | | 17 | 14 | 14 | | | |
| Example 7 | Compound 7 | | | | | | | 15 | 17 | 18 |
| Example 8 | Compound 8 | | | | | | | 13 | 12 | 11 |
| Example 9 | Compound 4 | | | | | | | 16 | 18 | 16 |
| Example 10 | Mixture 3 | | | | | | | 9 | 7 | 7 |
| Comparative example 1 | Dimenthylglutaric acid | 22 | 20 | 21 | 22 | 20 | 19 | 22 | 21 | 23 |
| Comparative example 2 | 1-Menthol | 6 | 24 | 25 | 7 | 24 | 25 | | | |

Numbers in Table are the total score of the ranking numbers.

As obvious from the results in Table 1, menthol showed the strongest cooling action after air drying for 10 minutes, but the action was found to be less consistent. On the other hand, the compounds of the invention showed long-lasting cooling action and the effects are better than that of dimenthylglutaric acid. In particular, the mixture of the compounds of the invention appeared to be excellent cooling action in the initial strength and the consistency.

Test Example 2

Test of a Cooling Towel (Washing Processed)

Each of Compounds 1 to 4 and 6 that were obtained by the above synthetic examples, Mixture 1 which is an equivalent-weight mixture of Compounds 1 to 4, Mixture 2 which is an equivalent-weight mixture of Compounds 5 to 8, Mixture 3 which is an equivalent-weight mixture of Compounds 2, 3 and 8, and l-menthoxypropanediol as a comparative compound was compounded with a base composition for washing detergent at a concentration of 1%, and then a pure cotton hand towel (white plain towel made in Japan, 20 cm×20 cm, degrease-finished) was hand-washed for three minutes by using the detergent at pre-determined concentration (water 10 L, detergent 3 g, and water temperature 17° C.). After rinsing with the same amount of water for 2 minutes, water was removed from the towel by brief squeezing, and then the towel was air-dried for 6 hours inside the building. The hand towel thus prepared and those after further air-dried for 24 hours or 48 hours were brought into contact with the inside of upper parts of arms, and the cooling action thereof was determined organoleptically. Results are shown in Table 2.

Meanwhile, the evaluation was carried out by five panelists having 5 years or longer experience. The above compounds, mixtures and menthoxypropanediol were divided into three groups of A to C (group A; Compound 1, mixture 1, Compound 2, menthoxypropanediol: group B; mixture 2, Compound 3, Compound 6, menthoxypropanediol: group C; Compound 8, Compound 4, mixture 3, menthoxypropanediol). Then, different 4 kinds of samples were ranked from the strongest to weakest in action respectively by the panelists in each three groups. The results are shown by the total score of the ranking numbers. The results are expressed by the total score of the rankings. In other words, smaller total score means to show a better cooling sensation effect.

TABLE 2

Results of comparison concern with lasting properties of cooling effect on treated hand towel after washing

|  | Materials | Group A After 6 hr | Group A After 24 hr | Group A After 48 hr | Group B After 6 hr | Group B After 24 hr | Group B After 48 hr | Group C After 6 hr | Group C After 24 hr | Group C After 48 hr |
|---|---|---|---|---|---|---|---|---|---|---|
| Example 11 | Compound 1 | 11 | 10 | 13 | | | | | | |
| Example 12 | Mixture 1 | 7 | 7 | 6 | | | | | | |
| Example 13 | Compound 2 | 13 | 11 | 12 | | | | | | |
| Example 14 | Mixture 2 | | | | 8 | 7 | 6 | | | |
| Example 15 | Compound 3 | | | | 11 | 10 | 10 | | | |
| Example 16 | Compound 6 | | | | 13 | 14 | 14 | | | |
| Example 17 | Compound 8 | | | | | | | 13 | 13 | 13 |
| Example 18 | Compound 4 | | | | | | | 10 | 12 | 11 |
| Example 19 | Mixture 3 | | | | | | | 7 | 5 | 7 |
| Comparative example 4 | Menthoxypropanediol | 19 | 20 | 19 | 18 | 19 | 20 | 19 | 20 | 19 |

Numbers in Table are the total score of the ranking numbers.

According to Table 2, it was found that overall the compounds of the invention showed an excellent cooling action compared with l-menthoxypropanediol and the effect was not weakened even after 48 hours. In addition, in terms of the effect, the mixture appeared to be better like Test example 1. Meanwhile, after the washing treatment and 6 hours of air drying, almost no cooling action was observed from l-menthoxypropanediol alone.

Example 20

Body Shampoo

A fragrance composition containing the sensory stimulation agent was produced from 35 parts by mass of the sensory stimulation agent composition containing the compound of the invention that were obtained from the above Synthetic examples and 65 parts by mass of a citrus-herbal mixed fragrance (manufactured by Takasago International Corporation), and eight kinds of body shampoos A to H were prepared according to the following prescription by using the fragrance composition (addition amount is based on parts by mass). The shampoos had excellent cool feeling and also were excellent in lasting property.

TABLE 3

Prescription for body shampoo

| Ingredients | A | B | C | D | E | F | G | H |
|---|---|---|---|---|---|---|---|---|
| Triethanolamine | 9.00 | 9.00 | 9.00 | 9.00 | 9.00 | 9.00 | 9.00 | 9.00 |
| Lauric acid | 6.00 | 6.00 | 6.00 | 6.00 | 6.00 | 6.00 | 6.00 | 6.00 |
| Myristic acid | 9.00 | 9.00 | 9.00 | 9.00 | 9.00 | 9.00 | 9.00 | 9.00 |
| Lauryl polyoxyethylene sulfosuccinate disodium salt (1 E.O.) (42%) | 10.00 | 10.00 | 10.00 | 10.00 | 10.00 | 10.00 | 10.00 | 10.00 |
| Alkyl (C8 to C16) glucoside | 8.00 | 8.00 | 8.00 | 8.00 | 8.00 | 8.00 | 8.00 | 8.00 |
| Glyceryl laurate | 1.00 | 1.00 | 1.00 | 1.00 | 1.00 | 1.00 | 1.00 | 1.00 |
| 2-Hydroxyethyl distearate | 2.50 | 2.50 | 2.50 | 2.50 | 2.50 | 2.50 | 2.50 | 2.50 |
| Coconut oil fatty acid diethanol amide | 3.00 | 3.00 | 3.00 | 3.00 | 3.00 | 3.00 | 3.00 | 3.00 |

TABLE 3-continued

Prescription for body shampoo

| Ingredients | A | B | C | D | E | F | G | H |
|---|---|---|---|---|---|---|---|---|
| Propylene glycol | 5.00 | 5.00 | 5.00 | 5.00 | 5.00 | 5.00 | 5.00 | 5.00 |
| Dibutylhydroxytoluene | 0.05 | 0.05 | 0.05 | 0.05 | 0.05 | 0.05 | 0.05 | 0.05 |
| Edetic acid disodium salt | 0.10 | 0.10 | 0.10 | 0.10 | 0.10 | 0.10 | 0.10 | 0.10 |
| Ethyl p-oxybenzoate | 0.20 | 0.20 | 0.20 | 0.20 | 0.20 | 0.20 | 0.20 | 0.20 |
| Methyl p-oxybenzoate | 0.10 | 0.10 | 0.10 | 0.10 | 0.10 | 0.10 | 0.10 | 0.10 |
| Fragrance composition containing the sensory stimulation agent comprising the following components | 1.00 | 1.00 | 1.00 | 1.00 | 1.00 | 1.00 | 1.00 | 1.00 |
| Citrus-herbal mixed fragrance | (0.65) | (0.65) | (0.65) | (0.65) | (0.65) | (0.65) | (0.65) | (0.65) |
| Compound 1 | (0.25) | | | | | | | |
| Compound 2 | | (0.25) | | | | | | |
| Compound 3 | | | (0.25) | | | | | |
| Compound 4 | | | | (0.25) | | | | |
| Compound 5 | | | | | (0.25) | | | |
| Compound 6 | | | | | | (0.25) | | |
| Compound 7 | | | | | | | (0.25) | |
| Compound 8 | | | | | | | | (0.25) |
| Mixture containing equal weight amount of Compounds 2, 3 and 8 | (0.10) | (0.10) | (0.10) | (0.10) | | | | |
| Mixture containing equal weight amount of Compounds 1 to 4 | | | | | (0.10) | (0.10) | (0.10) | (0.10) |
| Purified water (balance) | | | | | | | | |
| Total | 100.00 | 100.00 | 100.00 | 100.00 | 100.00 | 100.00 | 100.00 | 100.00 |

Example 21

Cooling Sensation Agent Composition

Seven kinds of cooling sensation agent compositions 1 to 7 were prepared according to the following prescription (addition amount is based on parts by mass) by mixing the compound of the invention that was obtained from the Synthetic examples above.

TABLE 4

Amount compounded

| Ingredients | Cooling sensation composition 1 | Cooling sensation Composition 2 | Cooling sensation Composition 3 | Cooling sensation Composition 4 | Cooling sensation Composition 5 | Cooling sensation Composition 6 | Cooling sensation Composition 7 |
|---|---|---|---|---|---|---|---|
| l-Isopulegol | 15 | 7.5 | 7.5 | 7.5 | 7.5 | | 7.5 |
| l-Menthoxy-propanediol | 35 | 17.5 | 17.5 | 17.5 | 17.5 | | 17.5 |
| l-Menthol | 30 | 20 | 20 | 20 | 20 | | 19.995 |
| p-Menthane-3,8-diol | 20 | 5 | 5 | 5 | 5 | | 5 |
| Vanillyl butyl ether | | | | | | | 0.0005 |
| Compound 1 | | 10 | | 10 | | 20 | 10 |
| Compound 2 | | 10 | | 10 | | 10 | 10 |
| Compound 3 | | 10 | | 10 | | 10 | 10 |
| Compound 4 | | 10 | | | 12.5 | 10 | |
| Compound 5 | | 10 | | | 12.5 | 10 | |
| Compound 6 | | | 10 | | 12.5 | 10 | |
| Compound 7 | | | 10 | | 12.5 | 10 | |
| Compound 8 | | | 30 | 20 | | 20 | 20 |
| Total | 100 | 100 | 100 | 100 | 100 | 100 | 100 |

Example 22

Lotion with Cooling Sensation Effect

Seven kinds of lotions A to G with cooling sensation effect were prepared according to the following prescription (addition amount is based on parts by mass) by using the seven cooling sensation agent compositions that were obtained from Example 21. Each of the lotions was sprayed by 1 g to a pure cotton hand towel (white plain towel made in Japan, 20 cm×20 cm, degrease-finished). Those which were air-dried for 3 hours or 8 hours were brought into contact with the inside of upper parts of arms, and the cooling action of the towel was determined organoleptically. Results are shown in Table 5. The lotions prepared by using the cooling sensation agent compositions 2 to 7 showed better lasting cooling sensation effect compared to the lotion prepared by using the cooling sensation agent composition 1.

TABLE 5

Prescription of lotion with cooling sensation effect

| Ingredients | A | B | C | D | E | F | G |
|---|---|---|---|---|---|---|---|
| 95% ethanol | 50 | 50 | 50 | 50 | 50 | 50 | 50 |
| Cooling sensation composition 1 | 0.5 | | | | | | |
| Cooling sensation composition 2 | | 0.5 | | | | | |
| Cooling sensation composition 3 | | | 0.5 | | | | |
| Cooling sensation composition 4 | | | | 0.5 | | | |
| Cooling sensation composition 5 | | | | | 0.5 | | |
| Cooling sensation composition 6 | | | | | | 0.5 | |
| Cooling sensation composition 7 | | | | | | | 0.5 |
| Purified water | balance | balance | balance | balance | balance | balance | balance |
| Total | 100 | 100 | 100 | 100 | 100 | 100 | 100 |
| Cooling sensation effect (after 3 hours) | ○ | ○ | ○ | ○ | ○ | Δ | ○ |
| Cooling sensation effect (after 8 hours) | X | Δ | Δ | ○ | Δ | Δ | ○ |

○: Strong cooling sensation effect was recognized.
Δ: Gentle cooling sensation effect was recognized.
X: Almost no cooling sensation effect was recognized.

Example 23

Deodorant

Six kinds of deodorant spray agents A to F with a cooling sensation effect were prepared according to the following prescription (addition amount is based on parts by mass) by using the cooling sensation agent compositions 2 to 7 that are obtained from Example 21. The deodorants prepared by using the cooling sensation agent compositions 2 to 7 had an excellent lasting cooling sensation effect.

TABLE 6

Prescription of deodorant

| Ingredients | A | B | C | D | E | F |
|---|---|---|---|---|---|---|
| Dipropylene glycol | 0.02 | 0.02 | 0.02 | 0.02 | 0.02 | 0.02 |
| Phenoxy ethanol | 0.05 | 0.05 | 0.05 | 0.05 | 0.05 | 0.05 |
| Anise aldehyde | 0.0003 | 0.0003 | 0.0003 | 0.0003 | 0.0003 | 0.0003 |
| Linalool | 0.01 | 0.01 | 0.01 | 0.01 | 0.01 | 0.01 |
| Musk T (manufactured by Takasago International Corporation) | 0.001 | 0.0001 | 0.0001 | 0.0001 | 0.0001 | 0.0001 |
| Heliotropin | 0.0001 | 0.0001 | 0.0001 | 0.0001 | 0.0001 | 0.0001 |
| Tesalon | 0.2 | 0.2 | 0.2 | 0.2 | 0.2 | 0.2 |
| Green tea extract | 0.3 | 0.3 | 0.3 | 0.3 | 0.3 | 0.3 |
| 95% Ethanol | 10 | 10 | 10 | 10 | 10 | 10 |
| Dipotassium hydrogen phosphate | 0.5 | 0.5 | 0.5 | 0.5 | 0.5 | 0.5 |

TABLE 6-continued

Prescription of deodorant

| Ingredients | Amounts compounded | | | | | |
|---|---|---|---|---|---|---|
| | A | B | C | D | E | F |
| Cooling sensation composition 2 | 0.5 | | | | | |
| Cooling sensation composition 3 | | 0.5 | | | | |
| Cooling sensation composition 4 | | | 0.5 | | | |
| Cooling sensation composition 5 | | | | 0.5 | | |
| Cooling sensation composition 6 | | | | | 0.5 | |
| Cooling sensation composition 7 | | | | | | 0.5 |
| Purified water | balance | balance | balance | balance | balance | balance |
| Total | 100 | 100 | 100 | 100 | 100 | 100 |

What is claimed is:

1. A cooling sensation agent composition comprising 1-menthyl-(1-menthoxyethyl) succinic ester.

2. The cooling sensation agent composition according to claim 1, which further comprises at least one cooling sensation substance other than 1-menthyl-(1-menthoxyethyl) succinic ester.

3. The cooling sensation agent composition according to claim 2, wherein the at least one cooling sensation substance other than 1-menthyl-(1-menthoxyethyl) succinic ester is selected from the group consisting of: menthol, menthone, camphor, pulegol, isopulegol, cineole, mint oil, peppermint oil, spearmint oil, eucalyptus oil, 3-(1-menthoxy)propane-1,2-diol, N-alkyl-p-menthane-3-carboxamide, 2-methyl-3-(1-menthoxy)propane-1,2-diol, p-menthane-3,8-diol, 2-(1-menthoxy)ethan-1-ol, 3-(1-menthoxy)propan-1-ol, 4-(1-menthoxy)butan-1-ol, menthyl 3-hydroxybutanoate, menthyl lactate, menthone glycerin ketal, N-methyl-2,2-isopropylmethyl-3-methylbutane amide and menthyl glyoxylate.

4. A sensory stimulation agent composition comprising 1-menthyl-(1-menthoxyethyl) succinic ester.

5. The sensory stimulation agent composition according to claim 4, which further comprises at least one kind of warming and pungent substances.

6. The sensory stimulation agent composition according to claim 5, wherein the warming and pungent substances are vanillyl ethyl ether, vanillyl propyl ether, vanillin propylene glycol acetal, ethylvanillin propylene glycol acetal, capsaicin, gingerol, vanillyl butyl ether, 4-(1-menthoxymethyl)-2-(3'-rnethoxy-4'-hydroxy-phenyl)-1, 3-dioxolane, pepper oil, pepperoleoresin, gingeroleoresin, nonylic acid vanillylamide, jamboo oleoresin, Zanthoxylum Piperitum Peel Extract, sanshool-I, sanshool-II, sanshoamide, black pepper extract, chavicine, piperine and spilanthol.

7. A flavor composition, or a fragrance composition, or a beverage, or a food product, or a perfume, or a cosmetic product, or a toiletry product, or a fiber product, or clothing, or a medicine, which comprises the cooling sensation agent composition according to claim 1.

8. A flavor composition, or a fragrance composition, or a beverage, or a food product, or a perfume, or a cosmetic product, or a toiletry product, or a fiber product, or clothing or a medicine, which comprises the sensory stimulation agent composition according to claim 3.

9. A method for providing a long-lasting cooling sensation effect which comprises:
directly applying the fragrance composition, or the perfume or the cosmetic product, or the medicine, or the toiletry product according to claim 7 onto a skin or a scalp;
applying the flavor composition, or the fragrance composition, or the perfume, or the cosmetic product, or the toilet product, or the medicine according to claim 7 to a fiber product;
applying the fragrance composition, or the perfume according to claim 7 to clothing; or
administering the medicine according to claim 7 to an oral cavity.

10. A method for providing a long-lasting cooling sensation effect which comprises:
directly applying the fragrance composition, or the perfume, or cosmetic product, or the medicine, or the toiletry product according to claim 8 onto a skin or a scalp;
applying the flavor composition, or fragrance composition, the perfume or the cosmetic product, the toiletry product, or the medicine according to claim 8 to a fiber product;
applying the fragrance composition, or the perfume according to claim 8 to clothing; or
administering the medicine according to claim 8 to an oral cavity.

11. The flavor composition or the fragrance composition according to claim 7, wherein the content of the cooling sensation agent composition is 0.0001 to 90% by mass to the total mass of the composition.

12. The flavor composition or the fragrance composition according to claim 8, wherein the content of the sensory stimulation agent composition is 0.0001 to 90% by mass to the total mass of the composition.

13. The beverage, or the food product, or the perfume or the cosmetic product, or the toiletry product, or the fiber product, or the clothing or the medicine according to claim 7, wherein the content of the cooling sensation agent composition is $1 \times 10^{-7}$% to 20% by mass.

14. The beverage, or the food product, or the perfume or cosmetic product, or the toiletry product, or the fiber product, or the clothing, or the medicine according to claim 8, wherein the content of the sensory stimulation agent composition is $1 \times 10^{-7}$% to 20% by mass.

15. A cool refreshment processing method of a fiber product or clothing, which comprises compounding the cooling sensation agent composition according to claim 1 with the fiber product or the clothing.

16. A cool refreshment processing method of a fiber product, or clothing, which comprises compounding the sensory stimulation agent composition according to claim 3 with the fiber product or the clothing.

17. A method for producing a flavor composition, or a fragrance composition, or a beverage, or a food product, or a perfume, or a cosmetic product, or a toiletry product, or a fiber product, or clothing or a medicine, which comprises compounding the flavor composition, or the fragrance composition, or the beverage, or the food product, or the perfume, or the cosmetic product, or the toiletry product, or the fiber product, of the clothing, or the medicine with the cooling sensation agent composition according to claim 1.

18. A method for producing a flavor composition, or fragrance composition, or a beverage, or a food product, or a perfume or a cosmetic product, or a toiletry product, or a fiber product, or clothing, or a medicine, which comprises compounding the flavor composition, or the fragrance composition, or the beverage, or the food product, or the perfume, or the cosmetic product, or the toiletry product, or the fiber product, of the clothing, or the medicine with the sensory stimulation agent composition according to claim 3.

* * * * *